(12) United States Patent
Singh

(10) Patent No.: US 7,658,945 B2
(45) Date of Patent: *Feb. 9, 2010

(54) COMPOSITIONS FOR DELIVERING HYPNOTIC AGENTS ACROSS THE ORAL MUCOSA AND METHODS OF USE THEREOF

(75) Inventor: Nikhilesh N. Singh, Mill Valley, CA (US)

(73) Assignee: Transcept Pharmaceuticals, Inc., Pt. Richmond, CA (US)

( * ) Notice: Subject to any disclaimer, the term of this patent is extended or adjusted under 35 U.S.C. 154(b) by 588 days.

This patent is subject to a terminal disclaimer.

(21) Appl. No.: 11/060,641

(22) Filed: Feb. 16, 2005

(65) Prior Publication Data

US 2005/0226925 A1     Oct. 13, 2005

Related U.S. Application Data

(60) Provisional application No. 60/598,629, filed on Aug. 3, 2004, provisional application No. 60/608,957, filed on Feb. 17, 2004.

(51) Int. Cl.
*A61K 9/20* (2006.01)
*A61F 13/00* (2006.01)

(52) U.S. Cl. .................. 424/464; 424/434; 424/435
(58) Field of Classification Search .................. None
See application file for complete search history.

(56) References Cited

U.S. PATENT DOCUMENTS

| 4,382,938 A | 5/1983 | Kaplan et al. |
| 4,405,647 A | 9/1983 | Fisher et al. |
| 4,460,592 A | 7/1984 | Kaplan et al. |
| 4,808,594 A | 2/1989 | George et al. |
| 4,863,737 A | 9/1989 | Stanley et al. |

(Continued)

FOREIGN PATENT DOCUMENTS

WO    WO 99/16417 A1    4/1999

(Continued)

OTHER PUBLICATIONS

Danjou et al., "A comparison of the residual effects of zaleplon and zolpidem following administration 5 to 2 hours before awakening." Br. J. Clin. Pharmacology 48:367-374 (Jun. 1999).

(Continued)

*Primary Examiner*—Humera N Sheikh
(74) *Attorney, Agent, or Firm*—O'Melveny & Myers LLP

(57) ABSTRACT

The present invention provides novel compositions for the delivery of a hypnotic agent across the oral mucosa. In particular, the buffer system in the compositions of the present invention raises the pH of saliva to a pH greater than about 7.8, thereby facilitating the substantially complete conversion of the hypnotic agent from its ionized to its un-ionized form. As a result, the dose of hypnotic agent is rapidly and efficiently absorbed by the oral mucosa with surprisingly low inter-subject variability. Furthermore, delivery of the hypnotic agent across the oral mucosa advantageously bypasses hepatic first pass metabolism of the drug and avoids enzymatic degradation of the drug within the gastrointestinal tract. Methods for using the compositions of the present invention for treating sleep disorders such as insomnia are also provided.

26 Claims, 10 Drawing Sheets

U.S. PATENT DOCUMENTS

| | | |
|---|---|---|
| 5,132,114 A | 7/1992 | Stanley et al. |
| 5,178,878 A | 1/1993 | Wehling et al. |
| 5,223,264 A | 6/1993 | Wehling et al. |
| 5,284,659 A | 2/1994 | Cherukuri et al. |
| 5,288,497 A | 2/1994 | Stanley et al. |
| 5,288,498 A | 2/1994 | Stanley et al. |
| 5,503,846 A | 4/1996 | Wehling et al. |
| 5,686,094 A | 11/1997 | Acharya |
| 5,719,197 A | 2/1998 | Kanios et al. |
| 5,785,989 A | 7/1998 | Stanley et al. |
| 5,855,908 A | 1/1999 | Stanley et al. |
| 5,869,082 A | 2/1999 | Dugger, III |
| 5,895,664 A | 4/1999 | Cherukuri et al. |
| 5,955,098 A | 9/1999 | Dugger, III |
| 5,965,162 A | 10/1999 | Fuisz et al. |
| 6,024,981 A | 2/2000 | Khankari et al. |
| 6,110,486 A | 8/2000 | Dugger, III |
| 6,197,334 B1 | 3/2001 | Renda |
| 6,200,604 B1 | 3/2001 | Pather et al. |
| 6,210,699 B1 | 4/2001 | Acharya et al. |
| 6,211,392 B1 | 4/2001 | Fang et al. |
| 6,218,397 B1 | 4/2001 | Chen |
| 6,242,460 B1 | 6/2001 | Ettema et al. |
| 6,264,981 B1 | 7/2001 | Zhang et al. |
| 6,264,987 B1 | 7/2001 | Wright et al. |
| 6,280,770 B1 | 8/2001 | Pather et al. |
| 6,344,222 B1 | 2/2002 | Cherukuri et al. |
| 6,348,485 B1 | 2/2002 | Ohklawa et al. |
| 6,350,470 B1 | 2/2002 | Pather et al. |
| 6,358,060 B2 | 3/2002 | Pinney et al. |
| 6,368,625 B1 | 4/2002 | Siebert et al. |
| 6,383,471 B1 | 5/2002 | Chen et al. |
| 6,391,335 B1 | 5/2002 | Pather et al. |
| 6,441,018 B2 | 8/2002 | Faraci et al. |
| 6,509,036 B2 | 1/2003 | Pather et al. |
| 6,514,531 B1 * | 2/2003 | Alaux et al. ............... 424/468 |
| 6,569,463 B2 | 5/2003 | Patel et al. |
| 6,576,250 B1 | 6/2003 | Pather et al. |
| 6,586,478 B2 * | 7/2003 | Ackman et al. ............ 514/738 |
| 6,589,556 B2 | 7/2003 | Cherukuri |
| 6,624,162 B2 | 9/2003 | Uchida et al. |
| 6,638,535 B2 | 10/2003 | Lemmens et al. |
| 6,641,838 B2 | 11/2003 | Pather |
| 6,676,931 B2 | 1/2004 | Dugger, III. |
| 6,692,771 B2 | 2/2004 | Pather et al. |
| 6,720,001 B2 | 4/2004 | Chen et al. |
| 6,753,011 B2 * | 6/2004 | Faour ........................ 424/473 |
| 6,759,059 B1 | 7/2004 | Pettersson et al. |
| 6,761,910 B1 | 7/2004 | Pettersson et al. |
| 6,764,696 B2 | 7/2004 | Pather et al. |
| 6,893,654 B2 | 5/2005 | Pinney et al. |
| 6,923,988 B2 | 8/2005 | Patel et al. |
| 6,969,508 B2 | 11/2005 | Dugger, III |
| 6,977,070 B2 | 12/2005 | Dugger, III |
| 6,998,110 B2 | 2/2006 | Dugger, III |
| 7,163,705 B2 | 1/2007 | Johnson et al. |
| 2001/0051186 A1 | 12/2001 | Acharya et al. |
| 2002/0098264 A1 | 7/2002 | Cherukuri et al. |
| 2003/0077227 A1 | 4/2003 | Dugger, III |
| 2003/0077228 A1 | 4/2003 | Dugger, III |
| 2003/0077229 A1 | 4/2003 | Dugger, III |
| 2003/0082107 A1 | 5/2003 | Dugger, III |
| 2003/0091629 A1 | 5/2003 | Pather et al. |
| 2003/0095925 A1 | 5/2003 | Dugger, III |
| 2003/0095926 A1 | 5/2003 | Dugger, III |
| 2003/0095927 A1 | 5/2003 | Dugger, III |
| 2003/0124184 A1 | 7/2003 | Mezaache et al. |
| 2003/0185761 A1 | 10/2003 | Dugger, III |
| 2003/0185884 A1 | 10/2003 | Singh et al. |
| 2003/0190286 A1 | 10/2003 | Dugger, III |
| 2003/0211047 A1 | 11/2003 | Dugger, III |
| 2003/0232080 A1 | 12/2003 | Pather et al. |
| 2004/0062716 A1 | 4/2004 | Dugger, III |
| 2004/0120895 A1 | 6/2004 | Dugger, III |
| 2004/0120896 A1 | 6/2004 | Dugger, III |
| 2004/0136913 A1 | 7/2004 | Dugger, III |
| 2004/0136914 A1 | 7/2004 | Dugger, III |
| 2004/0136915 A1 | 7/2004 | Dugger, III |
| 2004/0141923 A1 | 7/2004 | Dugger, III |
| 2004/0185097 A1 | 9/2004 | Kanman et al. |
| 2004/0213855 A1 | 10/2004 | Pettersson |
| 2004/0258750 A1 | 12/2004 | Alaux et al. |
| 2004/0265239 A1 | 12/2004 | Dugger, III |
| 2004/0265375 A1 | 12/2004 | Platteeuw et al. |
| 2005/0002867 A1 | 1/2005 | Dugger, III |
| 2005/0025712 A1 | 2/2005 | Dugger, III |
| 2005/0025713 A1 | 2/2005 | Dugger, III |
| 2005/0025714 A1 | 2/2005 | Dugger, III |
| 2005/0025715 A1 | 2/2005 | Dugger, III |
| 2005/0025716 A1 | 2/2005 | Dugger, III |
| 2005/0025717 A1 | 2/2005 | Dugger, III |
| 2005/0031677 A1 | 2/2005 | Pather et al. |
| 2005/0037072 A1 | 2/2005 | Pather et al. |
| 2005/0038042 A1 | 2/2005 | Codd et al. |
| 2005/0042281 A1 | 2/2005 | Singh et al. |
| 2005/0142197 A1 | 6/2005 | Moe |
| 2005/0142198 A1 | 6/2005 | Moe |
| 2005/0164987 A1 | 7/2005 | Barberich |
| 2005/0281752 A1 | 12/2005 | Dugger, III |
| 2006/0216352 A1 | 9/2006 | Nystrom et al. |

FOREIGN PATENT DOCUMENTS

| | | |
|---|---|---|
| WO | WO 99/63977 | 12/1999 |
| WO | WO 00/16750 | 3/2000 |
| WO | WO 00/33835 | 6/2000 |
| WO | WO 00/38649 | 7/2000 |
| WO | WO 01/89476 A1 | 11/2001 |
| WO | WO 2005/032519 A1 | 4/2005 |
| WO | WO 2006/046041 A1 | 5/2006 |

OTHER PUBLICATIONS

Hindmarch et al., "Residual effects of zaleplon and zolpidem following middle of the night administration five hours to one hour before awakening." Human Psychopharmacology 16: pp. 159-167 (2001).

Werth et al., "Dynamics of the sleep EEG after an early evening nap: experimental data and simulations." American Physiological Society pp. R501-R510 (1996).

Ambien® patient information, downloaded from http://www.ambien.com/Consumer/utility/ambienPatient.pdf on Jun. 7, 2005.

Avdeef, A., "Physicochemical profiling (solubility, permeability and charge state)." Curr. Top. Med. Chem., 1(4):277-351 (2001).

Galey, W.R. et al., "The in vitro permeability of skin and buccal mucosa to selected drugs and tritiated water." J. Invest. Dermatol., 67(6):713-717 (1976).

Gandhi R. B. and J.R. Robinson, "Bioadhesion in drug delivery." Indian J. Pharm. Sci., 50(3):145-152 (1988).

Greenblatt, D.J. et al., "Kinetic and dynamic interaction study of zolpidem with ketoconazole, itraconazole, and fluconazole." Clin. Pharmacol. Ther., 64:661-671 (1998).

Greenblatt, D.J. et al., "Comparative kinetics and dynamics of zaleplon, zolpidem, and placebo." Clin. Pharmacol. Ther., 64:553-561 (1998).

Harris, D. et al., "Drug delivery via the mucous membranes of the oral cavity." J. Pharm. Sci., 81(1):1-10 (1992).

Holm, K.J. and K.L. Goa, "Zolpidem: an update of its pharmacology, therapeutic efficacy and tolerability in the treatment of insomnia." Drugs, 59:865-889 (2000).

Kansy, M. et al., "Physicochemical high throughput screening: parallel artificial membrane permeation assay in the description of passive absorption processes." J. Med. Chem., 41:1007-1010 (1998).

Nail, S. L. et al., "Fundamentals of freeze-drying", Pharm. Biotechnol., 14:281-360 (2002).

Rathbone, M. et al., "The oral cavity as a site for systemic drug delivery." *Adv. Drug Deliv. Rev.*, 13(1):1-22 (1994).

Squier, C.A. et al., "Lipid content and water permeability of skin and oral mucosa." *J. Invest. Dermatol.*, 96(1):123-126 (1991).

Squier, C.A. et al., in Oral Mucosal Drug Delivery, M. J. Rathbone (Ed.) (Marcel Dekker, Inc., New York, New York, pp. 1-26, 1996).

Tabak, L.A. et al., "Role of salivary mucins in the protection of the oral cavity." *J. Oral Pathol.*, 11(1):1-17 (1982).

Thapa, P. et al., "Lyophililization of unit dose pharmaceutical dosage forms." *Drug. Dev. Ind. Pharm.*, 29(5):595-602 (2003).

Wertz, P.W. et al., "Cellular and molecular basis of barrier function in oral epithelium." *Crit. Rev. Ther. Drug Carrier Syst.*, 8(3):237-269 (1991).

Doghramji, K. "The Need for Flexibility in Dosing of Hypnotic Agents" Sleep 23 (Supplement 1): S16-S22 (2000).

Fry, J. "Zaleplon improves sleep without producing rebound effects in outpatients with insomnia" International Clinical Pharmacology 15(3): 141-152 (2000).

Lader, M.H. "Implications of hypnotic flexibility on patterns of clinical use" UCP Supplement 116: 14-19 (Jan. 2001).

Merlotti, L. et al. "The Dose Effects of Zolpidem on the Sleep of Healthy Normals" J. Clinical Psychopharmacology 9(1): 9-14 (Feb. 1989).

Mitler, M.M. "Nonselective and Selective Benzodiazepine Receptor Agonists—Where Are We Today?" Sleep 23 (Supplement 1): S39-S47 (2000).

Scharf, M.B. "Individualizing therapy for early, middle-of-the-night and late-night insomnia" UCP Supplement 116: 20-24 (Jan. 2001).

Shangold, G. et al. "NovaDel NDA for Nitroglycerin Lingual Spray Is Accepted for Review by FDA" Khandaker Analytical Review 3(5): 28-30 (2004).

Walsh, J.K. et al. "Lack of Residual Sedation Following Middle-of-the-Night Zaleplon Administration in Sleep Maintenance Insomnia" Clin. Neuropharmacology 23(1): 17-21 (2000).

\* cited by examiner

COMPOSITIONS FOR DELIVERING HYPNOTIC AGENTS ACROSS THE ORAL MUCOSA AND METHODS OF USE THEREOF

CROSS-REFERENCES TO RELATED APPLICATIONS

The present application claims the benefit of U.S. Provisional Application No. 60/608,957, filed Feb. 17, 2004, and U.S. Provisional Application No. 60/598,629, filed Aug. 3, 2004, each of which is herein incorporated by reference in its entirety for all purposes.

BACKGROUND OF THE INVENTION

Insomnia is a condition that affects a person's ability to fall asleep or to maintain sleep. It is the most common sleep disorder, affecting millions of Americans each year. Benzodiazepines, which are available as short, intermediate, or long-acting hypnotic agents, have proven useful in treating insomnia. These benzodiazepines are thought to bind non-selectively to benzodiazepine$_1$ (omega$_1$,) and benzodiazepine$_2$ (omega$_2$) receptors. This non-selective binding may be responsible for some of the potential problems associated with the use of benzodiazepine compounds as hypnotics. For example, some benzodiazepines are thought to interfere with memory, cognition, and psychomotor function. In addition, problems with altered sleep architecture, rebound insomnia, hangover effects, and abuse potential have been reported with benzodiazepine use.

Selective benzodiazepine$_1$ receptor agonists have been developed and studied. For example, zolpidem (Ambien®; Searle and Co.) and zaleplon (Sonata®; Wyeth-Ayerst Co.) are non-benzodiazepine sedative agents thought to selectively bind to benzodiazepine (BZ$_1$) receptors. Zolpidem, an imidazopyridine, has been demonstrated to reduce sleep latency, increase sleep duration, and reduce nighttime awakenings. In addition, zolpidem has been found to preserve stage III and stage IV sleep, and to result in less disruption of REM (Rapid Eye Movement) sleep. Zaleplon is a pyrazolopyrimidine derivative, which has also proven useful as a hypnotic agent. However, zolpidem and zaleplon are both poorly soluble in aqueous media.

Typically, these hypnotic agents are delivered as oral dosages, which are formulated, for example, as tablets or capsules that are swallowed. Oral administration, however, has several disadvantages, such as drug losses during hepatic first pass metabolism, during enzymatic degradation within the GI tract, and during absorption. These drug losses not only increase the variability in drug response, but also often require that the medicament be given in greater initial doses. In addition, because the drug has to pass through the gastrointestinal system in order to enter the blood stream, the time to reach a therapeutic effect may be quite long, typically around forty-five minutes or longer.

Accordingly, other routes of drug administration have been investigated, including those involving transport across the mucous membranes. Of the various mucous membranes (e.g., oral, rectal, vaginal, ocular, nasal, etc.), drug delivery via the mucous membranes in the oral cavity seems to be the most easily tolerated by patients. In addition to avoiding the problems with traditional oral administration, drug delivery via the mucous membranes of the oral cavity has certain other advantages, due to the properties of the oral mucosa itself. For example, the mucous membranes of the oral cavity are highly vascularized and well supplied with lymphatic drainage sites.

In general, the mucous membranes of the oral cavity can be divided into five main regions: the floor of the mouth (sublingual), the cheeks (buccal), the gums (gingival), the roof of the mouth (palatal), and the lining of the lips. These regions differ from each other with respect to their anatomy, drug permeability, and physiological response to drugs. For example, in terms of permeability, sublingual is more permeable than buccal, which is more permeable than palatal. This permeability is generally based on the relative thickness and degree of keratinization of these membranes, with the sublingual mucosa being relatively thin and non-keratinized, the buccal mucosa being thicker and non-keratinized, and the palatal mucosa being intermediate in thickness, but keratinized.

In addition to the differences in permeability of the various mucous membranes, the extent of drug delivery is also affected by the properties of the drug to be delivered. The ability of a molecule to pass through any mucous membrane is dependent upon its size, its lipid solubility, and the extent to which it is ionized, among other factors.

The extent to which a drug is ionized has further been investigated with respect to drug delivery across the mucous membranes. Ionization is dependent on the dissociation constant (pKa), and the pH of the molecule's surrounding environment. In its un-ionized form, a drug is sufficiently lipophilic to traverse a membrane via passive diffusion. In fact, according to the pH partition hypothesis, only un-ionized, non-polar drugs will penetrate a lipid membrane.

At equilibrium, the concentrations of the un-ionized form of the drug are equal on both sides of the membrane. As the concentration gradient drives passive diffusion, an increase in the percentage of the un-ionized form of a drug correspondingly increases the transmucosal absorption of the drug. Maximum absorption across the membrane is thought to occur when a drug is 100% in its un-ionized form. Similarly, absorption across the membrane decreases as the extent of ionization increases. Therefore, one may influence the extent of drug absorption across the mucous membranes of the oral cavity by altering the salivary pH.

Some of the known transmucosal dosage forms include the use of a single buffering agent in order to change the pH of the saliva and tissues surrounding the buccal mucosa. However, these single buffering agents typically react with an acid or a base to create a final pH that is dependent upon the initial pH of the saliva of the user. A buffering agent used to attain a final pH that is dependent upon the initial pH of the user results in great variability. The extent of ionization, and hence the extent of absorption across the mucous membranes cannot be predicted with any sort of accuracy. This may pose significant problems when calculating precise doses, minimizing variability in patient response, and proving consistency in drug loading to the regulatory authorities. In addition, a single buffering agent is typically not capable of sustaining a given pH over a period of time for optimal absorption. While others in the art have disclosed the use of more than one buffering agent, these aforementioned problems are not easily cured by the nonchalant addition of an extra buffering agent, which may be unsafe and cause irreversible damage to the mucous membranes of the oral cavity. As such, a buffering system capable of achieving and sustaining a final pH independent of the initial pH in order to increase transmucosal absorption has not heretofore been demonstrated.

Similarly, a buffer system that facilitates substantially complete conversion of the ionized form of a drug to the un-ionized form in the shortest period of time, which is critical for producing rapid delivery of practically an entire drug dose across the oral mucosa, has not heretofore been demonstrated. Previous dosage forms resulted in great variability in drug delivery, due to the variability in the rates in which a drug was released from its carrier. That is, the rates of drug release in previously described chewing gums or lozenges are largely dependent upon the rate of chewing or sucking of the user. The variability in these rates from user to user further exacerbates the ability to predict the final amount of drug that will enter systemic circulation. In addition, the rate of drug release from the carrier is further dependent upon the ability of the drug to be released therefrom. Often times, the carrier (e.g., gum base) strongly adheres to the drug, making portions of the drug unavailable for absorption.

Accordingly, there is a need in the art for compositions for delivering hypnotic agents across the oral mucosa having buffer systems that facilitate absorption of the agents in a safe and stable manner. Similarly, there is a need in the art for compositions for delivering hypnotic agents across the oral mucosa having a buffer system that produces a final pH, independent of the initial pH, and sustains that final pH for a given period of time. In addition, there is a need in the art for compositions capable of rapidly facilitating substantially complete conversion of the hypnotic agent from its ionized to its un-ionized form. The present invention satisfies these and other needs.

BRIEF SUMMARY OF THE INVENTION

The present invention provides novel compositions for the delivery of a hypnotic agent across the oral mucosa. In particular, the buffer system in the compositions of the present invention raises the pH of saliva to a pH greater than about 7.8, thereby facilitating the substantially complete conversion of the hypnotic agent from its ionized to its un-ionized form. As a result, the dose of hypnotic agent is rapidly and efficiently absorbed by the oral mucosa with surprisingly low inter-subject variability (e.g., lower variability than absorption across the gut in the same patients). Furthermore, delivery of the hypnotic agent across the oral mucosa advantageously bypasses hepatic first pass metabolism of the drug and avoids enzymatic degradation of the drug within the gastrointestinal tract. Methods for using the compositions of the present invention for treating sleep disorders such as insomnia are also provided.

As such, in one aspect, the present invention provides a solid composition for delivery of a hypnotic agent across the oral mucosa, the composition comprising:
  (a) a hypnotic agent selected from the group consisting of an imidazopyridine, a dihydropyrrolopyrazine, a pyrazolopyrimidine, and a pharmaceutically acceptable salt thereof;
  (b) a carrier that provides complete buccal or sublingual disintegration in about 5 minutes or less following administration to the mouth; and
  (c) a binary buffer system comprising a carbonate salt and a bicarbonate salt, wherein the binary buffer system raises the pH of saliva to a pH greater than about 7.8, irrespective of the starting pH of saliva.

In another aspect, the present invention provides a composition for delivery of a hypnotic agent across the oral mucosa, the composition comprising:
  (a) a hypnotic agent selected from the group consisting of an imidazopyridine, a dihydropyrrolopyrazine, a pyrazolopyrimidine, and a pharmaceutically acceptable salt thereof;
  (b) a carrier; and
  (c) a binary buffer system comprising a carbonate salt and a bicarbonate salt, wherein the binary buffer system raises the pH of saliva to a pH greater than about 7.8, irrespective of the starting pH of saliva.

In yet another aspect, the present invention provides a composition for delivery of a hypnotic agent across the oral mucosa, the composition comprising:
  (a) a hypnotic agent selected from the group consisting of an imidazopyridine, a dihydropyrrolopyrazine, a pyrazolopyrimidine, and a pharmaceutically acceptable salt thereof;
  (b) a carrier; and
  (c) a binary buffer system comprising a carbonate salt or a bicarbonate salt and a second buffering agent, wherein the binary buffer system raises the pH of saliva to a pH greater than about 7.8, irrespective of the starting pH of saliva.

In still yet another aspect, the present invention provides a composition for delivery of a hypnotic agent across the oral mucosa, the composition comprising:
  (a) a hypnotic agent selected from the group consisting of an imidazopyridine, a dihydropyrrolopyrazine, a pyrazolopyrimidine, and a pharmaceutically acceptable salt thereof;
  (b) a carrier; and
  (c) a binary buffer system comprising a metal oxide and a citrate, phosphate, or borate salt, wherein the binary buffer system raises the pH of saliva to a pH greater than about 7.8, irrespective of the starting pH of saliva.

In a further aspect, the present invention provides a composition for delivery of a hypnotic agent across the oral mucosa, the composition comprising:
  (a) a hypnotic agent selected from the group consisting of an imidazopyridine, a dihydropyrrolopyrazine, a pyrazolopyrimidine, and a pharmaceutically acceptable salt thereof;
  (b) a carrier; and
  (c) a ternary buffer system comprising a carbonate salt, a bicarbonate salt, and a third buffering agent, wherein the ternary buffer system raises the pH of saliva to a pH greater than about 7.8, irrespective of the starting pH of saliva.

In another aspect, the present invention provides a composition for delivery of a hypnotic agent across the oral mucosa, the composition comprising:
  (a) a hypnotic agent selected from the group consisting of an imidazopyridine, a dihydropyrrolopyrazine, a pyrazolopyrimidine, and a pharmaceutically acceptable salt thereof;
  (b) a carrier; and
  (c) a buffer system comprising a carbonate salt or a bicarbonate salt and two or more buffering agents selected from the group consisting of a metal oxide, a citrate salt, a phosphate salt, and a borate salt, wherein the buffer system raises the pH of saliva to a pH greater than about 7.8, irrespective of the starting pH of saliva.

In yet another aspect, the present invention provides a method for treating a sleep disorder in a subject in need thereof, the method comprising:
  administering to the subject a composition comprising a therapeutically effective amount of a hypnotic agent selected from the group consisting of an imidazopyridine, a dihydropyrrolopyrazine, a pyrazolopyrimidine, and a pharmaceutically acceptable salt thereof; a carrier; and a binary buffer system comprising a carbonate salt and a bicarbonate salt, wherein the binary buffer system raises the pH of saliva to a pH greater than about 7.8, irrespective of the starting pH of saliva.

Other objects, features, and advantages of the present invention will be apparent to one of skill in the art from the following detailed description and figures.

DETAILED DESCRIPTION OF THE INVENTION

I. Definitions

Figure 1:
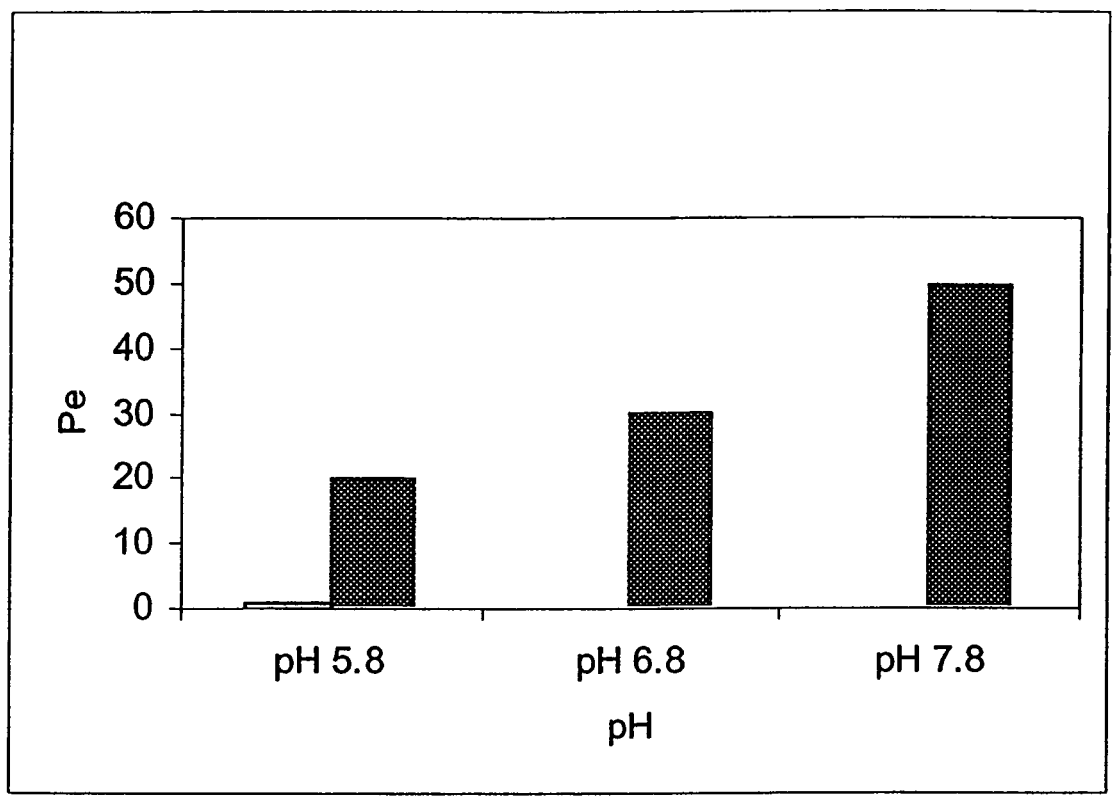
FIG. 1 is a bar chart illustrating the relationship between the pH and membrane permeation for zolpidem tartrate.

As used herein, the following terms have the meanings ascribed to them unless specified otherwise.

The term "sleep disorder" refers to a disruptive pattern of sleep arising from many causes including, without limitation, dysfunctional sleep mechanisms, abnormalities in physiological functions during sleep, abnormalities of the biological clock, and sleep disturbances that are induced by factors extrinsic to the sleep process. In particular, the term encompasses disorders associated with difficulties in staying asleep and/or falling asleep such as insomnia (e.g., transient, short-term, and chronic), delayed sleep phase syndrome, hypnotic-dependent sleep disorder, and stimulant-dependent sleep disorder; disorders associated with difficulties in staying awake such as sleep apnea, narcolepsy, restless leg syndrome, obstructive sleep apnea, central sleep apnea, idiopathic hypersomnia, respiratory muscle weakness-associated sleep disorder; disorders associated with difficulties in adhering to a regular sleep schedule such as sleep state misperception, shift work sleep disorder, chronic time zone change syndrome, and irregular sleep-wake syndrome; disorders associated with abnormal behaviors such as sleep terror disorder (i.e., parasomnia) and sleepwalking (i.e., somnambulism); and other disorders such as sleep bruxism, fibromyalgia, and nightmares.

The term "insomnia" refers to a sleep disorder characterized by symptoms including, without limitation, difficulty in falling asleep, difficulty in staying asleep, intermittent wakefulness, and/or waking up too early. The term also encompasses daytime symptoms such as sleepiness, anxiety, impaired concentration, impaired memory, and irritability. Types of insomnia suitable for treatment with the compositions of the present invention include, without limitation, transient, short-term, and chronic insomnia. The term "transient insomnia" refers to insomnia lasting for a few nights. The term "short-term insomnia" refers to insomnia lasting for about two to about four weeks. The term "chronic insomnia" refers to insomnia lasting for at least one month.

The terms "therapeutic agent" and "drug" are used interchangeably herein to refer to a substance having a pharmaceutical, pharmacological, psychosomatic, or therapeutic effect. Preferably, the therapeutic agent or drug is a hypnotic agent. Suitable hypnotic agents for use in the present invention include, without limitation, an imidazopyridine compound such as zolpidem or alpidem; a dihydropyrrolopyrazine compound such as zopeclon; a pyrazolopyrimidine compound such as zaleplon or indiplon; pharmaceutically acceptable salts thereof; and combinations thereof. In a particularly preferred embodiment, the hypnotic agent is zolpidem, in all suitable forms.

The term "therapeutically effective amount" refers to the amount of a hypnotic agent that is capable of achieving a therapeutic effect in a subject in need thereof. For example, a therapeutically effective amount of a hypnotic agent can be the amount that is capable of preventing or relieving one or more symptoms associated with a sleep disorder.

The term "bioavailability" refers to the rate and/or extent to which a drug is absorbed or becomes available to the treatment site in the body.

The terms "disintegration" and "dissolution" are used interchangeably herein to refer to the reduction of a solid dosage form of the present invention to a liquid form. More particularly, a complete disintegration or dissolution of a solid dosage form refers to less than about 25% by weight of the solid dosage form remaining in the mouth following an appropriate time period, e.g., 5 minutes or less, after administration. Suitable methods known in the art for determining the disintegration profile of a solid dosage form include, e.g., the United States Pharmacopeia (USP) disintegration test. Suitable methods known in the art for determining the dissolution profile of a solid dosage form include, e.g., USP dissolution tests such as USP <711>Apparatus 1 or USP <711>Apparatus 2.

As used herein, the phrase "substantially complete conversion of the hypnotic agent from its ionized to its un-ionized form" refers to greater than about 50% conversion of the hypnotic agent from its ionized form into its un-ionized form. For example, the buffer system may favor at least about 50%, 55%, 60%, 65%, 70%, 75%, 80%, 85%, 90%, 95%, or 99% conversion of the hypnotic agent from its ionized form into its un-ionized form. In some embodiments, the conversion occurs within about 10 minutes following administration.

The term "variability" refers to inter-subject variability in terms of the percent of relative standard deviation (RSD) for the maximum plasma concentration ($C_{max}$) and the time to reach the maximum plasma concentration ($T_{max}$). Notably, the compositions of the present invention have an RSD for $C_{max}$ of about 27% versus about 45% for commercial oral tablets such as Ambien® tablets. Further, the compositions of the present invention have an RSD for $T_{max}$ of about 50% versus about 100% for commercial oral tablets such as Ambien® tablets.

The term "administering" refers to administration of the compositions of the present invention to the mucous membranes of the oral cavity (i.e., oral mucosa). Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. Preferably, the compositions of the present invention are administered to the sublingual mucosa, buccal mucosa, or a combination thereof.

II. General

The present invention provides novel compositions for the delivery of a hypnotic agent across the oral mucosa. In particular, the buffer system in the compositions of the present invention raises the pH of saliva to a pH greater than about 7.8, thereby facilitating the substantially complete conversion of the hypnotic agent from its ionized to its un-ionized form. As a result, the dose of hypnotic agent is rapidly and efficiently absorbed by the oral mucosa with surprisingly low inter-subject variability in terms of maximum plasma concentration ($C_{max}$) and the time to reach the maximum plasma concentration ($T_{max}$). Furthermore, delivery of the hypnotic agent across the oral mucosa advantageously bypasses hepatic first pass metabolism of the drug and avoids enzymatic degradation of the drug within the gastrointestinal tract, resulting in increased bioavailability of the hypnotic agent and reduced time to onset of therapeutic activity as compared to traditional dosage forms for oral (e.g., tablet) administration. Methods for using the compositions of the present invention for treating sleep disorders such as various types of insomnia are also provided.

The present invention is based upon the surprising discovery that sublingual delivery of zolpidem compositions containing the buffer systems described herein provides both increased bioavailability of the therapeutic agent and reduced time to onset of therapeutic activity that far surpass those observed for commercial oral tablets such as Ambien® tablets and buccal tablets such as zolpidem FlashDose® tablets (Biovail Technologies Ltd.; Chantilly, Va.). In fact, it was counterintuitive to expect that the rapidly disintegrating zolpidem solid dosage forms described herein would provide the rapid absorption and marked increase in bioavailability of zolpidem that was observed. As a result, the zolpidem in the compositions of the present invention reaches the systemic circulation in a substantially shorter period of time and at a substantially higher concentration than the zolpidem in either of the commercial tablet compositions. Thus, the zolpidem compositions of the present invention are superior to the commercial tablet compositions in reducing the time to onset of therapeutic activity, maintaining sleep (e.g., total sleep time, number of awakenings), enhancing sleep quality, eliminating the effect of food, and reducing any morning-after residual effects.

III. Description of the Embodiments

In one aspect, the present invention provides a solid composition for delivery of a hypnotic agent across the oral mucosa, the composition comprising:

(a) a hypnotic agent selected from the group consisting of an imidazopyridine, a dihydropyrrolopyrazine, a pyrazolopyrimidine, and a pharmaceutically acceptable salt thereof, (b) a carrier that provides complete buccal or sublingual disintegration in about 5 minutes or less following administration to the mouth; and (c) a binary buffer system comprising a carbonate salt and a bicarbonate salt, wherein the binary buffer system raises the pH of saliva to a pH greater than about 7.8, irrespective of the starting pH of saliva.

In certain instances, the binary buffer system raises the pH of saliva to a pH greater than about 8.5, irrespective of the starting pH of saliva. In certain other instances, the binary buffer system raises the pH of saliva to a pH greater than about 9 (e.g., about 9-11), irrespective of the starting pH of saliva. In one embodiment, the imidazopyridine hypnotic agent is selected from the group consisting of zolpidem and alpidem. Preferably, the imidazopyridine hypnotic agent is zolpidem. Any form of zolpidem is suitable for use in the compositions described herein, e.g., a salt form of zolpidem (e.g., zolpidem tartrate), a free base form of zolpidem, or a mixture thereof. In another embodiment, the dihydropyrrolopyrazine hypnotic agent is zopeclon. In yet another embodiment, the pyrazolopyrimidine hypnotic agent is selected from the group consisting of zaleplon and indiplon.

In certain instances, the carrier provides complete buccal or sublingual disintegration in about 2 minutes or less following administration. In certain other instances, the carrier comprises at least one binder and at least one disintegrating agent in such relative proportion to provide a buccal or sublingual disintegration time of about 5 minutes or less, preferably about 2 minutes or less, following administration. Preferably, the ratio of the binder to the disintegrating agent is from about 0.1 to about 10.0, more preferably from about 0.1 to about 1.0, and most preferably from about 0.26 to about 0.79. However, one skilled in the art will appreciate that the compositions of the present invention can be made without any binders, e.g., to produce a highly friable dosage form.

In another embodiment, the carbonate salt is selected from the group consisting of sodium carbonate, potassium carbonate, calcium carbonate, ammonium carbonate, and magnesium carbonate. In yet another embodiment, the bicarbonate salt is selected from the group consisting of sodium bicarbonate, potassium bicarbonate, calcium bicarbonate, ammonium bicarbonate, and magnesium bicarbonate. In a preferred embodiment, the binary buffer system comprises sodium carbonate and sodium bicarbonate. In another preferred embodiment, the sodium bicarbonate is dessicant-coated sodium bicarbonate.

In yet another embodiment, the compositions of the present invention are in a dosage form selected from the group consisting of a lozenge, a chewing gum; a chewable tablet, and a dissolving tablet such as a slow-dissolving tablet or a quick-dissolving tablet. Preferably, the composition is a lozenge or a dissolving tablet. A description of lozenge, chewing gum, chewable tablet, slow-dissolving tablet, and quick-dissolving tablet compositions containing a hypnotic agent is provided in the Examples below.

In a preferred embodiment, the hypnotic agent is delivered across an oral mucosa selected from the group consisting of the sublingual mucosa, the buccal mucosa, and a combination thereof. In a particularly preferred embodiment, the composition is administered sublingually so that the hypnotic agent is delivered across the sublingual mucosa.

In another embodiment, the carrier is selected from the group consisting of a binder, a gum base, and combinations thereof. Suitable binders for use in the compositions of the present invention include, without limitation, sugar alcohols such as mannitol, sorbitol, and xylitol; sugars such as lactose, dextrose, sucrose, glucose, and powdered sugar; natural gums such as acacia gum, xanthan gum, guar gum, tara gum, mesquite gum, fenugreek gum, locust bean gum, ghatti gum, and tragacanth gum; other substances such as inositol, molasses, maltodextrin, starch, cellulose, microcrystalline cellulose, polyvinylpyrrolidone, alginate, extract of Irish moss, panwar gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol; and combinations thereof. Suitable gum bases for use in the compositions of the present invention include, for example, materials selected from among the many water-insoluble and saliva-insoluble gum base materials known in the art. In certain instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000).

In yet another embodiment, the compositions of the present invention can further comprise a sweetening agent, a flavoring agent, a protecting agent, a plasticizer, a wax, an elastomeric solvent, a filler material, a preservative, or combinations thereof. In still yet another embodiment, the compositions of the present invention can further comprise a lubricating agent, a wetting agent, an emulsifying agent, a solubilizing agent, a suspending agent, a coloring agent, a disintegrating agent, or combinations thereof. In a preferred embodiment, the average particle size of the drug in the compositions described herein is about 20 microns, as compared to a typical average drug particle size of from about 75 to about 100 microns. In another preferred embodiment, the average particle size of the drug in the compositions described herein is less than or equal to the average particle size of the carrier ingredients (e.g., gum base, binders, etc.).

In preferred embodiments of the present invention, the hypnotic agent is zolpidem and the binary buffer system comprises sodium carbonate and sodium bicarbonate. Such compositions are preferably formulated in the form of a lozenge, candy, or dissolving tablet (e.g., slow-dissolving tablet or quick-dissolving tablet) for sublingual administration. As a result, upon sublingual administration, zolpidem is delivered across the sublingual mucosa. In other preferred embodiments, the sodium bicarbonate is dessicant-coated sodium bicarbonate. A combined weight percent of sodium carbonate and sodium bicarbonate that is greater than or equal to the weight percent of zolpidem is also preferred.

In certain instances, the composition comprises from about 1.0 to about 5.5 weight percent zolpidem; from about 6.0 to about 10.0 weight percent sodium carbonate; and from about 9.0 to about 13.0 weight percent dessicant-coated sodium bicarbonate. In a preferred embodiment, the composition comprises about 4.5 weight percent zolpidem; about 8.0 weight percent sodium carbonate; and about 11.0 weight percent dessicant-coated sodium bicarbonate. Such compositions are preferably in the form of a lozenge or candy with a mass of from about 100 to about 300 mg, e.g., about 100, 110, 120, 130, 140, 150, 160, 170, 180, 190, 200, 210, 220, 230, 240, 250, 260, 270, 280, 290, and 300 mg. The lozenges or candies dissolve in a subject's mouth at a very rapid rate, e.g., within about 2-3 minutes following administration.

In certain other instances, the composition comprises from about 1.0 to about 5.0 weight percent zolpidem; from about 5.0 to about 9.0 weight percent sodium carbonate; and from about 7.0 to about 11.0 weight percent sodium bicarbonate. In a preferred embodiment, the composition comprises about 4.0 weight percent zolpidem; about 7.0 weight percent sodium carbonate; and about 9.0 weight percent sodium bicarbonate. Such compositions are preferably in the form of a dissolving tablet such as a slow-dissolving tablet or a quick-dissolving tablet of from about 100 to about 300 mg, e.g., about 100, 110, 120, 130, 140, 150, 160, 170, 180, 190, 200, 210, 220, 230, 240, 250, 260, 270, 280, 290, and 300 mg. The quick-dissolving tablets dissolve in a subject's mouth at a rapid rate, e.g., within about 5 minutes following administration, and the slow-dissolving tablets dissolve in a subject's mouth at a slower rate, e.g., within about 10 minutes following administration.

In another aspect, the present invention provides a composition for delivery of a hypnotic agent across the oral mucosa, the composition comprising:

(a) a hypnotic agent selected from the group consisting of an imidazopyridine, a dihydropyrrolopyrazine, a pyrazolopyrimidine, and a pharmaceutically acceptable salt thereof;

(b) a carrier; and (c) a binary buffer system comprising a carbonate salt and a bicarbonate salt, wherein the binary buffer system raises the pH of saliva to a pH greater than about 7.8, irrespective of the starting pH of saliva.

In certain instances, the binary buffer system raises the pH of saliva to a pH greater than about 8.5, irrespective of the starting pH of saliva. In certain other instances, the binary buffer system raises the pH of saliva to a pH greater than about 9 (e.g., about 9-11), irrespective of the starting pH of saliva. Suitable imidazopyridine, dihydropyrrolopyrazine, and pyrazolopyrimidine hypnotic agents for use in the present invention are described above. Suitable carbonate salts and bicarbonate salts for use in the binary buffer systems of the present invention are also described above.

In another embodiment, the compositions of the present invention are in any of the dosage forms described above. Preferably, the hypnotic agent is delivered across an oral mucosa as described above. In yet another embodiment, the carrier is selected from the group consisting of a binder, a gum base, and combinations thereof. Suitable binders and gum bases for use in the compositions of the present invention are described above. In certain instances, the carrier provides a buccal or sublingual disintegration time of about 10 minutes or less, preferably about 5 minutes or less, and more preferably about 2 minutes or less, following administration. In certain other instances, the carrier comprises at least one binder and at least one disintegrating agent in such relative proportion to provide a buccal or sublingual disintegration time of about 10 minutes or less, preferably about 5 minutes or less, and more preferably about 2 minutes or less, following administration.

In yet another embodiment, the compositions of the present invention can further comprise one or more of the additional agents described above. In preferred embodiments, the average particle size of the drug in the compositions described herein is about 20 microns and/or is less than or equal to the average particle size of the carrier ingredients (e.g., gum base, binders, etc.).

In other preferred embodiments of the present invention, the hypnotic agent is zolpidem and the binary buffer system comprises sodium carbonate and sodium bicarbonate. Preferred amounts of each of these components is described above, along with preferred dosage forms and their preferred weight.

In yet another aspect, the present invention provides a composition for delivery of a hypnotic agent across the oral mucosa, the composition comprising:
(a) a hypnotic agent selected from the group consisting of an imidazopyridine, a dihydropyrrolopyrazine, a pyrazolopyrimidine, and a pharmaceutically acceptable salt thereof;
(b) a carrier; and
(c) a binary buffer system comprising a carbonate salt or a bicarbonate salt and a second buffering agent, wherein the binary buffer system raises the pH of saliva to a pH greater than about 7.8, irrespective of the starting pH of saliva.

In certain instances, the binary buffer system raises the pH of saliva to a pH greater than about 8.5, irrespective of the starting pH of saliva. In certain other instances, the binary buffer system raises the pH of saliva to a pH greater than about 9 (e.g., about 9-11), irrespective of the starting pH of saliva. Suitable imidazopyridine, dihydropyrrolopyrazine, and pyrazolopyrimidine hypnotic agents for use in the present invention are described above. Suitable carbonate salts and bicarbonate salts for use in the binary buffer systems of the present invention are also described above.

In one embodiment, the second buffering agent is selected from the group consisting of a metal oxide, a citrate salt, a phosphate salt, a borate salt, an ascorbate salt, an acetate salt, and alkaline starch. Suitable metal oxides include, without limitation, magnesium oxide and aluminum oxide. Preferably, the magnesium oxide is amorphous magnesium oxide. Suitable citrate, phosphate, and borate salts include, without limitation, any salt of citric acid, phosphoric acid, or boric acid known in the art. For example, in some embodiments, the citrate salt is selected from the group consisting of sodium citrate, potassium citrate, calcium citrate, magnesium citrate, and ammonium citrate. In other embodiments, the phosphate salt is selected from the group consisting of monobasic sodium phosphate, dibasic sodium phosphate, monobasic potassium phosphate, dibasic potassium phosphate, monobasic calcium phosphate, dibasic calcium phosphate, monobasic magnesium phosphate, dibasic magnesium phosphate, monobasic ammonium phosphate, and dibasic ammonium phosphate. In yet other embodiments, the borate salt is selected from the group consisting of sodium borate, potassium borate, calcium borate, magnesium borate, and ammonium borate. In certain instances, the binary buffer system comprises a carbonate salt and a metal oxide, a citrate salt, a phosphate salt, or a borate salt. In certain other instances, the binary buffer system comprises a bicarbonate salt and a metal oxide, a citrate salt, a phosphate salt, or a borate salt.

In another embodiment, the compositions of the present invention are in any of the dosage forms described above. Preferably, the hypnotic agent is delivered across an oral mucosa as described above. In yet another embodiment, the carrier is selected from the group consisting of a binder, a gum base, and combinations thereof. Suitable binders and gum bases for use in the compositions of the present invention are described above. In certain instances, the carrier provides a buccal or sublingual disintegration time as described above. In certain other instances, the carrier comprises at least one binder and at least one disintegrating agent as described above.

In yet another embodiment, the compositions of the present invention can further comprise one or more of the additional agents described above. In preferred embodiments, the average particle size of the drug in the compositions described herein is about 20 microns and/or is less than or equal to the average particle size of the carrier ingredients (e.g., gum base, binders, etc.).

In preferred embodiments of the present invention, the hypnotic agent is zolpidem and the binary buffer system comprises sodium carbonate or sodium bicarbonate and a second buffering agent. Such compositions are preferably formulated in the form of a lozenge, candy, or dissolving tablet for sublingual administration.

In still yet another aspect, the present invention provides a composition for delivery of a hypnotic agent across the oral mucosa, the composition comprising:
(a) a hypnotic agent selected from the group consisting of an imidazopyridine, a dihydropyrrolopyrazine, a pyrazolopyrimidine, and a pharmaceutically acceptable salt thereof;
(b) a carrier; and
(c) a binary buffer system comprising a metal oxide and a citrate, phosphate, or borate salt, wherein the binary buffer system raises the pH of saliva to a pH greater than about 7.8, irrespective of the starting pH of saliva.

In certain instances, the binary buffer system raises the pH of saliva to a pH greater than about 8.5, irrespective of the starting pH of saliva. In certain other instances, the binary buffer system raises the pH of saliva to a pH greater than about 9 (e.g., about 9-11), irrespective of the starting pH of saliva. Suitable imidazopyridine, dihydropyrrolopyrazine, and pyrazolopyrimidine hypnotic agents for use in the present invention are described above.

Suitable metal oxides include, without limitation, magnesium oxide and aluminum oxide. Suitable citrate, phosphate, and borate salts include, without limitation, any salt of citric acid, phosphoric acid, or boric acid known in the art such as those described above. In certain instances, the binary buffer system comprises a metal oxide and a citrate salt. In certain other instances, the binary buffer system comprises a metal oxide and a phosphate salt. In further instances, the binary buffer system comprises a metal oxide and a borate salt.

In one embodiment, the compositions of the present invention are in any of the dosage forms described above. Preferably, the hypnotic agent is delivered across an oral mucosa as described above. In yet another embodiment, the carrier is selected from the group consisting of a binder, a gum base, and combinations thereof. Suitable binders and gum bases for use in the compositions of the present invention are described above. In certain instances, the carrier provides a buccal or sublingual disintegration time as described above. In certain other instances, the carrier comprises at least one binder and at least one disintegrating agent as described above.

In another embodiment, the compositions of the present invention can further comprise one or more of the additional agents described above. In preferred embodiments, the average particle size of the drug in the compositions described herein is about 20 microns and/or is less than or equal to the average particle size of the carrier ingredients (e.g., gum base, binders, etc.).

In preferred embodiments of the present invention, the hypnotic agent is zolpidem and the binary buffer system comprises amorphous magnesium oxide and a citrate, phosphate, or borate salt. Such compositions are preferably formulated in the form of a lozenge, candy, or dissolving tablet for sublingual administration.

In a further aspect, the present invention provides a composition for delivery of a hypnotic agent across the oral mucosa, the composition comprising:
  (a) a hypnotic agent selected from the group consisting of an imidazopyridine, a dihydropyrrolopyrazine, a pyrazolopyrimidine, and a pharmaceutically acceptable salt thereof,
  (b) a carrier; and
  (c) a ternary buffer system comprising a carbonate salt, a bicarbonate salt, and a third buffering agent, wherein the ternary buffer system raises the pH of saliva to a pH greater than about 7.8, irrespective of the starting pH of saliva.

In certain instances, the binary buffer system raises the pH of saliva to a pH greater than about 8.5, irrespective of the starting pH of saliva. In certain other instances, the binary buffer system raises the pH of saliva to a pH greater than about 9 (e.g., about 9-11), irrespective of the starting pH of saliva. Suitable imidazopyridine, dihydropyrrolopyrazine, and pyrazolopyrimidine hypnotic agents for use in the present invention are described above. Suitable carbonate salts and bicarbonate salts for use in the ternary buffer systems of the present invention are also described above.

In one embodiment, the third buffering agent is selected from the group consisting of a metal oxide, a citrate salt, a phosphate salt, a borate salt, an ascorbate salt, an acetate salt, and alkaline starch. Suitable metal oxides include, without limitation, magnesium oxide and aluminum oxide. Suitable citrate, phosphate, and borate salts include, without limitation, any salt of citric acid, phosphoric acid, or boric acid known in the art such as those described above. In certain instances, the ternary buffer system comprises a carbonate salt, a bicarbonate salt, and a metal oxide. In certain other instances, the ternary buffer system comprises a carbonate salt, a bicarbonate salt, and a citrate, phosphate, or borate salt.

In another embodiment, the compositions of the present invention are in any of the dosage forms described above. Preferably, the hypnotic agent is delivered across an oral mucosa as described above. In yet another embodiment, the carrier is selected from the group consisting of a binder, a gum base, and combinations thereof. Suitable binders and gum bases for use in the compositions of the present invention are described above. In certain instances, the carrier provides a buccal or sublingual disintegration time as described above. In certain other instances, the carrier comprises at least one binder and at least one disintegrating agent as described above.

In yet another embodiment, the compositions of the present invention can further comprise one or more of the additional agents described above. In preferred embodiments, the average particle size of the drug in the compositions described herein is about 20 microns and/or is less than or equal to the average particle size of the carrier ingredients (e.g., gum base, binders, etc.).

In preferred embodiments of the present invention, the hypnotic agent is zolpidem and the ternary buffer system comprises sodium carbonate, sodium bicarbonate, and a third buffering agent. Such compositions are preferably formulated in the form of a lozenge, candy, or dissolving tablet for sublingual administration. In instances where the third buffering agent is a metal oxide, a weight percent of the metal oxide that is greater than the combined weight percent of sodium carbonate and sodium bicarbonate is preferred.

In another aspect, the present invention provides a composition for delivery of a hypnotic agent across the oral mucosa, the composition comprising:
  (a) a hypnotic agent selected from the group consisting of an imidazopyridine, a dihydropyrrolopyrazine, a pyrazolopyrimidine, and a pharmaceutically acceptable salt thereof;
  (b) a carrier; and
  (c) a buffer system comprising a carbonate salt or a bicarbonate salt and two or more buffering agents selected from the group consisting of a metal oxide, a citrate salt, a phosphate salt, and a borate salt, wherein the buffer system raises the pH of saliva to a pH greater than about 7.8, irrespective of the starting pH of saliva.

In certain instances, the binary buffer system raises the pH of saliva to a pH greater than about 8.5, irrespective of the starting pH of saliva. In certain other instances, the binary 5 buffer system raises the pH of saliva to a pH greater than about 9 (e.g., about 9-11), irrespective of the starting pH of saliva. Suitable imidazopyridine, dihydropyrrolopyrazine, and pyrazolopyrimidine hypnotic agents for use in the present invention are described above. Suitable carbonate salts and bicarbonate salts for use in the buffer systems of the present invention are also described above.

Suitable metal oxides include, without limitation, magnesium oxide and aluminum oxide. Suitable citrate, phosphate, and borate salts include, without limitation, any salt of citric acid, phosphoric acid, or boric acid known in the art such as those described above. In certain instances, the buffer system comprises a carbonate salt or a bicarbonate salt, a metal oxide, and a citrate, phosphate, or borate salt. In certain other instances, the buffer system comprises a carbonate salt or a bicarbonate salt, a citrate salt, and a phosphate salt. In certain instances, the buffer system comprises a carbonate salt or a bicarbonate salt, a citrate salt, and a borate salt. In certain other instances, the buffer system comprises a carbonate salt or a bicarbonate salt, a phosphate salt, and a borate salt.

In one embodiment, the compositions of the present invention are in any of the dosage forms described above. Preferably, the hypnotic agent is delivered across an oral mucosa as described above. In yet another embodiment, the carrier is selected from the group consisting of a binder, a gum base, and combinations thereof. Suitable binders and gum bases for use in the compositions of the present invention are described above. In certain instances, the carrier provides a buccal or sublingual disintegration time as described above. In certain other instances, the carrier comprises at least one binder and at least one disintegrating agent as described above.

In another embodiment, the compositions of the present invention can further comprise one or more of the additional agents described above. In preferred embodiments, the average particle size of the drug in the compositions described herein is about 20 microns and/or is less than or equal to the average particle size of the carrier ingredients (e.g., gum base, binders, etc.).

In preferred embodiments of the present invention, the hypnotic agent is zolpidem and the buffer system comprises sodium carbonate or sodium bicarbonate and two or more buffering agents selected from the group consisting of a metal oxide, a citrate salt, a phosphate salt, and a borate salt. Such compositions are preferably formulated in the form of a lozenge, candy, or dissolving tablet for sublingual administration.

In yet another aspect, the present invention provides a method for treating a sleep disorder in a subject in need thereof, the method comprising:

administering to the subject a composition comprising a therapeutically effective amount of a hypnotic agent selected from the group consisting of an imidazopyridine, a dihydropyrrolopyrazine, a pyrazolopyrimidine, and a pharmaceutically acceptable salt thereof; a carrier; and a binary buffer system comprising a carbonate salt and a bicarbonate salt, wherein the binary buffer system raises the pH of saliva to a pH greater than about 7.8, irrespective of the starting pH of saliva.

In a preferred embodiment, the composition delivers the hypnotic agent across the oral mucosa such as, for example, the sublingual mucosa, the buccal mucosa, or a combination thereof. In a particularly preferred embodiment, the composition is administered sublingually so that the hypnotic agent is delivered across the sublingual mucosa. Suitable sleep disorders that can be treated with the compositions of the present invention include, without limitation, insomnia such as transient insomnia, short-term insomnia, and chronic insomnia.

In certain instances, the binary buffer system raises the pH of saliva to a pH greater than about 8.5, irrespective of the starting pH of saliva. In certain other instances, the binary buffer system raises the pH of saliva to a pH greater than about 9 (e.g., about 9-11), irrespective of the starting pH of saliva. Suitable imidazopyridine, dihydropyrrolopyrazine, and pyrazolopyrimidine hypnotic agents for use in the present invention are described above. Suitable carbonate salts and bicarbonate salts for use in the binary buffer systems of the present invention are also described above.

In addition to a binary buffer system comprising a carbonate salt and a bicarbonate salt, other buffer systems are suitable for use in the compositions of the present invention. For example, in an alternative embodiment, the binary buffer system comprises a carbonate salt or a bicarbonate salt and a second buffering agent such as a metal oxide, a citrate salt, a phosphate salt, a borate salt, an ascorbate salt, an acetate salt, and alkaline starch. In another alternative embodiment, the binary buffer system comprises a metal oxide and a citrate, phosphate, or borate salt. In yet another alternative embodiment, the buffer system is a ternary buffer system comprising a carbonate salt, a bicarbonate salt, and a third buffering agent such as a metal oxide, a citrate salt, a phosphate salt, a borate salt, an ascorbate salt, an acetate salt, and alkaline starch. In still yet another alternative embodiment, the buffer system comprises a carbonate salt or a bicarbonate salt and two or more buffering agents selected from the group consisting of a metal oxide, a citrate salt, a phosphate salt, and a borate salt.

In one embodiment, the compositions of the present invention are in any of the dosage forms described above. Preferably, the hypnotic agent is delivered across an oral mucosa as described above. In yet another embodiment, the carrier is selected from the group consisting of a binder, a gum base, and combinations thereof. Suitable binders and gum bases for use in the compositions of the present invention are described above. In certain instances, the carrier provides a buccal or sublingual disintegration time as described above. In certain other instances, the carrier comprises at least one binder and at least one disintegrating agent as described above.

In another embodiment, the compositions of the present invention can further comprise one or more of the additional agents described above. In preferred embodiments, the average particle size of the drug in the compositions described herein is about 20 microns and/or is less than or equal to the average particle size of the carrier ingredients (e.g., gum base, binders, etc.).

In preferred embodiments of the present invention, the hypnotic agent is zolpidem and the binary buffer system comprises sodium carbonate and sodium bicarbonate. Preferred amounts of each of these components is described above, along with preferred dosage forms and their preferred weight.

A. Hypnotic Agents

The hypnotic agents of the present invention are preferably selected from an imidazopyridine compound such as zolpidem or alpidem; a dihydropyrrolopyrazine compound such as zopeclon; a pyrazolopyrimidine compound such as zaleplon or indiplon; pharmaceutically acceptable salts thereof; and combinations thereof. More preferably, the hypnotic agent is zolpidem, in all suitable forms.

In general, the hypnotic agents of the present invention are basic compounds having an ionized form and an un-ionized form. In certain instances, the hypnotic agent is initially present at least partly in an ionized form. In certain other instances, the hypnotic agent is initially present in an un-ionized form. As described in more detail below, the buffer system of the compositions described herein helps to convert substantially all of the hypnotic agent from its ionized form to its un-ionized form. Alternatively, the buffer system helps ensure that the hypnotic agent, initially in an un-ionized form, remains in an un-ionized form.

As used herein, the term "hypnotic agent" includes all pharmaceutically acceptable forms of the hypnotic agent being described. For example, the hypnotic agent can be in a racemic or isomeric mixture, a solid complex bound to an ion exchange resin, or the like. In addition, the hypnotic agent can be in a solvated form. The term "hypnotic agent" is also intended to include all pharmaceutically acceptable salts, derivatives, and analogs of the hypnotic agent being described, as well as combinations thereof. For example, the pharmaceutically acceptable salts of the hypnotic agent include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of the hypnotic agent is suitable for use in the compositions of the present invention, e.g., a pharmaceutically acceptable salt of the hypnotic agent (e.g., zolpidem tartrate), a free base of the hypnotic agent, or a mixture thereof.

Conversion of the ionized form to the un-ionized form for the hypnotic agent is related to pH according to the formula: $pH = pKa + \log_{10}$ (un-ionized concentration/ionized concentration). When the pH is the same as the pKa, equimolar concentrations of the un-ionized form and ionized form exist. For basic compounds such as the hypnotic agents described herein, when the pH is one unit higher than the pKa, the ratio of the un-ionized form to the ionized form is 91:9. Similarly, when the pH is two units higher than the pKa, the ratio of un-ionized form to the ionized form is 100:1. As noted above, the un-ionized form is lipophilic and, therefore, more capable of passing through mucous membranes such as the oral mucosa than the ionized form, which is lipophobic in nature. Accordingly, increasing the pH of the saliva favors conversion of the ionized form into the un-ionized form for basic compounds such as the hypnotic agents described herein, and the final pH can be determined by making use of the above formula.

The hypnotic agents of the present invention are selected from the class of compounds in the imidazopyridine, dihydropyrrolopyrazine, or pyrazolopyrimidine family and are useful in the treatment of conditions such as sleep disorders. Illustrative examples of suitable imidazopyridine compounds for use in the present invention are zolpidem, alpidem, pharmaceutically acceptable salts thereof, analogs thereof, and derivatives thereof. These imidazopyridine compounds each have an imidazopyridine group, as shown below:

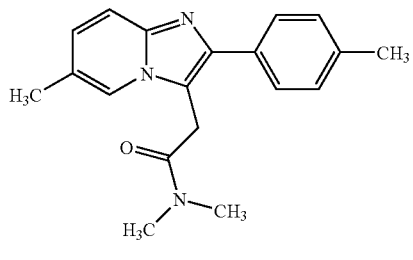

Zolpidem

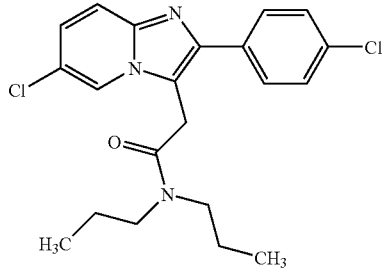

Alpidem

For the imidazopyridine compounds, the nitrogen in the imidazole portion of the bicyclic ring of the structure controls the extent of ionization and the degree of lipophilicity in any given medium. Typically the nitrogen in the imidazole portion imparts a pKa of from about 6.8 to about 7.5 to the molecule. Therefore, using the above formula, it can be demonstrated that about 90% conversion to an un-ionized form can be achieved for these compounds at a pH of from about 7.8 to about 8.5.

Illustrative examples of suitable dihydropyrrolopyrazine compounds for use in the present invention are zopeclon, pharmaceutically acceptable salts thereof, analogs thereof, and derivatives thereof. These dihydropyrrolopyrazines each have a dihydropyrrolopyrazine group, as shown below:

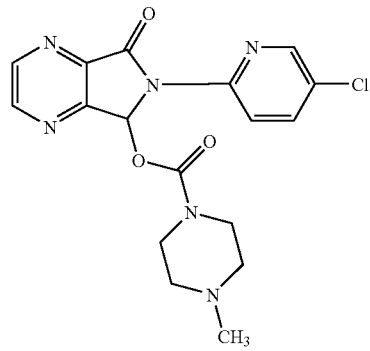

Zopeclon

Illustrative examples of suitable pyrazolopyrimidine compounds for use in the present invention are zaleplon, indiplon, pharmaceutically acceptable salts thereof, analogs thereof, and derivatives thereof. These pyrazolopyrimidines each have a pyrazolopyrimidine group, as shown below:

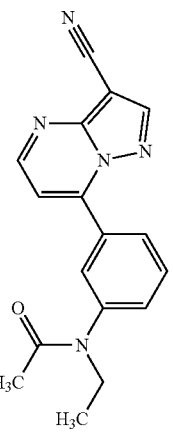

Zaleplon

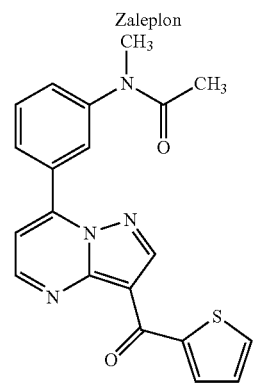

Indiplon

For the pyrazolopyrimidine compounds, the nitrogen in the pyrimidine group controls the extent of ionization and the degree of lipophilicity in any given medium. Typically, the nitrogen in the pyrimidine group imparts a pKa of from about 8 to about 9 to the molecule. Therefore, using the above formula, it can be demonstrated that about 90% conversion to an un-ionized form can be achieved for these compounds at a pH of from about 9 to about 10.

In general, the hypnotic agents of the present invention acts as benzodiazepine receptor agonists. Preferably, the hypnotic agents selectively bind to the benzodiazepine$_1$ receptor. Without being bound to any particular theory, the therapeutic activity of the hypnotic agents of the present invention in treating sleep disorders is attributed to an enhancement of the inhibitory action of gamma-aminobutyric acid (GABA) in the central nervous system.

B. Buffer Systems

The buffer systems of the compositions described herein are capable of raising the pH of saliva to a pH greater than about 7.8, irrespective of the starting pH of saliva. In this way, the buffer system helps convert substantially all of the hypnotic agent from its ionized form to its un-ionized form. Alternatively, the buffer system helps ensure that the hypnotic agent, initially in an un-ionized form, remains in an un-ionized form. Although basic buffering agents are typically used in the buffer systems of the present invention, one skilled in the art will appreciate that acidic agents can also be used to adjust the pH of the buffer system as long as the buffer system as a whole raises the pH of saliva to a pH greater than about 7.8.

In one embodiment, the present invention provides binary buffer systems comprising a carbonate salt and a bicarbonate salt. The concentration of each buffer system component is tailored such that the final salivary pH is achieved and sustained for a period of time, e.g., for at least about 2 minutes, at least about 5 minutes, at least about 10 minutes, at least about 20 minutes, or at least about 60 minutes. This typically involves a sensory and safety trial and error type of procedure of adding various amounts of each buffer system component and then measuring the final pH over time. In this way, selection of an appropriate weight ratio for each buffer system component can be easily determined in just a few trials. For example, the weight ratio of carbonate salt to bicarbonate salt can be from about 1:10 to about 10:1, preferably from about 1:5 to about 5:1, more preferably from about 1:3 to about 3:1, and still more preferably from about 1:2 to about 2:1.

The carbonate salt is generally selected from sodium carbonate, potassium carbonate, calcium carbonate, ammonium carbonate, and magnesium carbonate. Preferably, the carbonate salt is sodium carbonate or potassium carbonate. Most preferably, the carbonate salt is sodium carbonate. Similarly, the bicarbonate salt is generally selected from sodium bicarbonate, potassium bicarbonate, calcium bicarbonate, ammonium bicarbonate, and magnesium bicarbonate. Preferably, the bicarbonate salt is sodium bicarbonate or potassium bicarbonate. Most preferably, the bicarbonate salt is sodium bicarbonate. In some embodiments, a dessicant-coated sodium bicarbonate is preferred. The amount of carbonate salt and bicarbonate salt used in the binary buffer system is an amount that is sufficient to raise salivary pH to a pH of about 7.8 or more, preferably about 8.5 or more, and more preferably about 9 or more (e.g., about 9-11), irrespective of the starting pH.

In certain instances, the amount of bicarbonate salt is greater than or equal to the amount of carbonate salt, and the weight ratio of carbonate salt to bicarbonate salt is from about 1:1 to about 1:10, preferably from about 1:1 to about 1:5, and more preferably from about 1:1 to about 1:2, e.g., 1:1, 1:1.1, 1:1.2, 1:1.3, 1:1.4, 1:1.5, 1:1.6, 1:1.7, 1:1.8, 1:1.9, or 1:2. Alternatively, the amount of bicarbonate salt is less than or equal to the amount of carbonate salt, and the weight ratio of carbonate salt to bicarbonate salt is from about 1:1 to about 10:1, preferably from about 1:1 to about 5:1, and more preferably from about 1:1 to about 2:1, e.g., 1:1, 1.1:1, 1.2:1, 1.3:1, 1.4:1, 1.5:1, 1.6:1, 1.7:1, 1.8:1, 1.9:1, or 2:1. In certain other instances, the combined amount of carbonate salt and bicarbonate salt is greater than or equal to the amount of the hypnotic agent, and the weight ratio of carbonate salt and bicarbonate salt to hypnotic agent is preferably from about 1:1 to about 10:1, e.g., 1:1, 2:1, 3:1, 4:1, 5:1, 6:1, 7:1, 8:1, 9:1, or 10:1. Alternatively, the combined amount of carbonate salt and bicarbonate salt is less than or equal to the amount of the hypnotic agent, and the weight ratio of carbonate salt and bicarbonate salt to hypnotic agent is preferably from about 1:1 to about 1:10, e.g., 1:1, 1:2, 1:3, 1:4, 1:5, 1:6, 1:7, 1:8, 1:9, or 1:10.

In view of the above, the buffer systems of the present invention, in some of the most preferred embodiments, are binary buffer systems containing sodium carbonate and sodium bicarbonate.

Alternatively, in another embodiment, the buffer systems of the present invention are binary buffer systems comprising a carbonate salt or a bicarbonate salt and a second buffering agent. The concentration of each buffer system component is tailored such that the final salivary pH is achieved and sustained for a period of time, e.g., for at least about 2 minutes, at least about 5 minutes, at least about 10 minutes, at least about 20 minutes, or at least about 60 minutes.

Suitable carbonate salts and bicarbonate salts are described above. The amount of carbonate salt or bicarbonate salt used in the binary buffer system is an amount that is sufficient, when used with the second buffering agent, to raise salivary pH to a pH of about 7.8 or more, preferably about 8.5 or more, and more preferably about 9 or more (e.g., about 9-11), irrespective of the starting pH. In certain instances, the amount of the second buffering agent in the binary buffer system is greater than or equal to the amount of the carbonate salt or bicarbonate salt. For example, the weight ratio of the second buffering agent to the carbonate salt or bicarbonate salt can be from about 1:1 to about 10:1, preferably from about 1:1 to about 5:1, and more preferably from about 1:1 to about 3:1. In certain other instances, the amount of the second buffering agent in the binary buffer system is less than or equal to the amount of the carbonate salt or bicarbonate salt. For example, the weight ratio of the second buffering agent to the carbonate salt or bicarbonate salt can be from about 1:1 to about 1:10, preferably from about 1:1 to about 1:5, and more preferably from about 1:1 to about 1:3.

The second buffering agent is generally selected from a metal oxide such as magnesium oxide or aluminum oxide; a citrate salt such as sodium citrate, potassium citrate, calcium citrate, magnesium citrate, and ammonium citrate; a phosphate salt such as monobasic sodium phosphate, dibasic sodium phosphate, monobasic potassium phosphate, dibasic potassium phosphate, monobasic calcium phosphate, dibasic calcium phosphate, monobasic magnesium phosphate, dibasic magnesium phosphate, monobasic ammonium phosphate, and dibasic ammonium phosphate; a borate salt such as sodium borate, potassium borate, calcium borate, magnesium borate, and ammonium borate; an ascorbate salt such as potassium ascorbate or sodium ascorbate; an acetate salt such as potassium acetate or sodium acetate; and alkaline starch. However, one skilled in the art will appreciate that any metal oxide or salt of citric acid, phosphoric acid, boric acid, ascorbic acid, or acetic acid is suitable for use in the buffer systems of the present invention. The amount of the second buffering agent used in the binary buffer system is an amount that is sufficient, when used with the carbonate salt or bicarbonate salt, to raise salivary pH to a pH of about 7.8 or more, preferably about 8.5 or more, and more preferably about 9 or more (e.g., about 9-11), irrespective of the starting pH. In some embodiments, a metal oxide such as magnesium oxide or aluminum oxide is the preferred second buffering agent. In a particularly preferred embodiment, the metal oxide is amorphous magnesium oxide.

Alternatively, in yet another embodiment, the buffer systems of the present invention are binary buffer systems comprising a metal oxide and a citrate, phosphate, or borate salt. The concentration of each buffer system component is tailored such that the final salivary pH is achieved and sustained for a period of time, e.g., for at least about 2 minutes, at least 5 about minutes, at least about 10 minutes, at least about 20 minutes, or at least about 60 minutes.

Suitable metal oxides include, without limitation, magnesium oxide and aluminum oxide. Suitable citrate, phosphate, and borate salts include, without limitation, essentially any salt of citric acid, phosphoric acid, or boric acid known in the art such as those described above. In certain instances, the binary buffer system comprises a metal oxide and a citrate salt. In certain other instances, the binary buffer system comprises a metal oxide and a phosphate salt. In further instances, the binary buffer system comprises a metal oxide and a borate salt. The amount of the metal oxide used in the binary buffer system is an amount that is sufficient, when used with the citrate, phosphate, or borate salt, to raise salivary pH to a pH of about 7.8 or more, preferably about 8.5 or more, and more preferably about 9 or more (e.g., about 9-11), irrespective of the starting pH. Similarly, the amount of the citrate, phosphate, or borate salt used in the binary buffer system is an amount that is sufficient, when used with the metal oxide, to raise salivary pH to a pH of about 7.8 or more, preferably about 8.5 or more, and more preferably about 9 or more (e.g., about 9-11), irrespective of the starting pH.

In certain instances, the amount of the metal oxide in the binary buffer system is greater than or equal to the amount of the citrate, phosphate, or borate salt. For example, the weight ratio of the metal oxide to the citrate, phosphate, or borate salt can be from about 1:1 to about 10:1, preferably from about 1:1 to about 5:1, and more preferably from about 1:1 to about 3:1. In certain other instances, the amount of the metal oxide in the binary buffer system is less than or equal to the amount of the citrate, phosphate, or borate salt. For example, the weight ratio of the metal oxide to the citrate, phosphate, or borate salt can be from about 1:1 to about 1:10, preferably from about 1:1 to about 1:5, and more preferably from about 1:1 to about 1:3.

Alternatively, in still yet another embodiment, the buffer systems of the present invention are ternary buffer systems comprising a carbonate salt, a bicarbonate salt, and a third buffering agent. The concentration of each buffer system component is tailored such that the final salivary pH is achieved and sustained for a period of time, e.g., for at least about 2 minutes, at least 5 about minutes, at least about 10 minutes, at least about 20 minutes, or at least about 60 minutes. The procedure described above for determining an appropriate weight ratio for each buffer system component can also be applied to ternary buffer systems.

Suitable carbonate salts and bicarbonate salts are described above. The amount of carbonate salt and bicarbonate salt used in the ternary buffer system is an amount that is sufficient, when used with the third buffering agent, to raise salivary pH to a pH of about 7.8 or more, preferably about 8.5 or more, and more preferably about 9 or more (e.g., about 9-11), irrespective of the starting pH.

The third buffering agent is generally selected from a metal oxide, a citrate salt, a phosphate salt, a borate salt, an ascorbate salt such as potassium ascorbate or sodium ascorbate, an acetate salt such as potassium acetate or sodium acetate, and alkaline starch. Suitable metal oxides include, without limitation, magnesium oxide and aluminum oxide. Suitable citrate, phosphate, and borate salts include, without limitation, any salt of citric acid, phosphoric acid, or boric acid known in the art such as those described above. The amount of the third buffering agent used in the ternary buffer system is an amount that is sufficient, when used with the remaining components, to raise salivary pH to a pH of about 7.8 or more, preferably about 8.5 or more, and more preferably about 9 or more (e.g., about 9-11), irrespective of the starting pH. In some embodiments, a metal oxide such as magnesium oxide or aluminum oxide is the preferred third buffering agent. In a particularly preferred embodiment, the metal oxide is amorphous magnesium oxide.

In certain instances, the amount of the carbonate salt or bicarbonate salt in the ternary buffer system is greater than or equal to the amount of the third buffering agent. For example, the weight ratio of the carbonate salt or bicarbonate salt to the third buffering agent can be from about 1:1 to about 10:1, preferably from about 1:1 to about 5:1, and more preferably from about 1:1 to about 3:1. In certain other instances, the amount of the carbonate salt or bicarbonate salt in the ternary buffer system is less than or equal to the amount of the third buffering agent. For example, the weight ratio of the carbonate salt or bicarbonate salt to the third buffering agent can be from about 1:1 to about 1:10, preferably from about 1:1 to about 1:5, and more preferably from about 1:1 to about 1:3.

The ternary buffer systems of the present invention, in some of the most preferred embodiments, contain sodium carbonate, sodium bicarbonate, and amorphous magnesium oxide. In certain instances, the amount of sodium bicarbonate is greater than or equal to the amount of sodium carbonate. For example, the weight ratio of sodium bicarbonate to sodium carbonate can be from about 1:1 to about 10:1, preferably from about 1:1 to about 5:1, and more preferably from about 1:1 to about 3:1. In certain other instances, the amount of amorphous magnesium oxide is greater than or equal to the combined amount of sodium carbonate and sodium bicarbonate. For example, the weight ratio of amorphous magnesium oxide to sodium carbonate and sodium bicarbonate can be from about 1:1 to about 10:1, preferably from about 1:1 to about 5:1, and more preferably from about 1:1 to about 3:1.

Alternatively, in a further embodiment, the buffer systems of the present invention are buffer systems comprising a carbonate salt or a bicarbonate salt and two or more buffering agents selected from the group consisting of a metal oxide, a citrate salt, a phosphate salt, and a borate salt. The concentration of each buffer system component is tailored such that the final salivary pH is achieved and sustained for a period of time, e.g., for at least about 2 minutes, at least 5 about minutes, at least about 10 minutes, at least about 20 minutes, or at least about 60 minutes.

Suitable carbonate salts and bicarbonate salts are described above. The amount of carbonate salt or bicarbonate salt used in the buffer system is an amount that is sufficient, when used with the remaining components, to raise salivary pH to a pH of about 7.8 or more, preferably about 8.5 or more, and more preferably about 9 or more (e.g., about 9-11), irrespective of the starting pH.

The two or more buffering agents are generally selected from a metal oxide, a citrate salt, a phosphate salt, a borate salt, an ascorbate salt, an acetate salt, and alkaline starch. Suitable metal oxides include, without limitation, magnesium oxide and aluminum oxide. Suitable citrate, phosphate, borate, ascorbate, and acetate salts include, without limitation, essentially any salt of citric acid, phosphoric acid, boric acid, ascorbic acid, or acetic acid known in the art such as those described above. The amount of the additional buffering agents used in the buffer system is an amount that is sufficient, when used with the carbonate salt or bicarbonate salt, to raise salivary pH to a pH of about 7.8 or more, preferably about 8.5 or more, and more preferably about 9 or more (e.g., about 9-11), irrespective of the starting pH.

In certain instances, the buffer system comprises a carbonate salt or a bicarbonate salt, a metal oxide, and a citrate, phosphate, or borate salt. In certain other instances, the buffer system comprises a carbonate salt or a bicarbonate salt, a citrate salt, and a phosphate salt. In certain instances, the buffer system comprises a carbonate salt or a bicarbonate salt, a citrate salt, and a borate salt. In certain other instances, the buffer system comprises a carbonate salt or a bicarbonate salt, a phosphate salt, and a borate salt. Preferably, the metal oxide is amorphous magnesium oxide.

In certain instances, the amount of the carbonate salt or bicarbonate salt in the buffer system is greater than or equal to the amount of the metal oxide or the citrate, phosphate, or borate salt. For example, the weight ratio of the carbonate salt or bicarbonate salt to the metal oxide or the citrate, phosphate, or borate salt can be from about 1:1 to about 10:1, preferably from about 1:1 to about 5:1, and more preferably from about 1:1 to about 3:1. In certain other instances, the amount of the carbonate salt or bicarbonate salt in the buffer system is less than or equal to the amount of the metal oxide or the citrate, phosphate, or borate salt. For example, the weight ratio of the carbonate salt or bicarbonate salt to the metal oxide or the citrate, phosphate, or borate salt can be from about 1:1 to about 1:10, preferably from about 1:1 to about 1:5, and more preferably from about 1:1 to about 1:3.

While the foregoing discussion has focused on the ability of the buffer system to alter salivary pH to favor substantial conversion to the un-ionized form of a therapeutic agent, it is conceivable that the buffer system may also have subsidiary beneficial effects on the extent of absorption across the oral mucosa. For example, the buffer system may create a final salivary pH that in turn affects the molecular configuration of the therapeutic agent in a way in which absorption across the oral mucosa is increased. It is to be understood that these subsidiary beneficial effects of the buffer system are within the general scope of the buffer system and compositions herein described.

C. Dosage Forms

The compositions of the present invention may take the form of solid, semi-solid, lyophilized powder, or liquid dosage forms, such as, for example, tablets (e.g., chewable, slow-dissolving, quick-dissolving), pills, capsules, lozenges, gums, powders, solutions, suspensions, emulsions, aerosols, or the like. Preferably, the dosage form is a chewing gum, dissolving tablet, chewable tablet, candy, or lozenge.

While each subject or patient possesses unique factors that may affect the rate and extent of absorption of the therapeutic agents described herein, dosage forms such as chewing gums, chewable tablets, dissolving tablets, or lozenges containing a buffer system described herein offer advantages over the traditional dosage forms for oral administration (i.e., Ambien®). For example, each of these dosage forms avoids hepatic first pass metabolism, degradation within the gastrointestinal tract, and drug loss during absorption. Consequently, the amount of therapeutic agent required per dose is less than that which would be required if formulated, for example, in a pill or tablet for oral administration. Similarly, the bioavailability of the therapeutic agent is increased, thereby reducing the time to onset of therapeutic activity as compared to traditional dosage forms for oral administration (see, Example 5 below).

In addition, the preferred dosage forms of the present invention (e.g., chewing gums, chewable tablets, dissolving tablets, lozenges) containing a buffer system described herein offer advantages over dosage forms for oral mucosal administration that do not contain the buffer system (i.e., zolpidem FlashDose® tablet). Importantly, because the buffer system in the dosage forms of the present invention helps convert substantially all of the therapeutic agent from its ionized form to its un-ionized form, the bioavailability of the therapeutic agent is increased, thereby reducing the time to onset of therapeutic activity as compared to dosage forms for oral mucosal administration that do not contain the buffer system. For example, U.S. Patent Publication No. 2003/0165566 discloses that the buccally administered zolpidem FlashDoses® tablet has a pharmacokinetic profile similar to that observed for the orally administered Ambien® tablet. As such, the zolpidem compositions of the present invention surpass both commercial tablet compositions by providing an increase in the bioavailability of zolpidem and a reduction in the time to onset of therapeutic activity.

As used herein, the term "dosage form" refers to physically discrete units suitable as unitary dosages for human subjects and other mammals, each unit containing a predetermined quantity of therapeutic agent calculated to produce the desired onset, tolerability, and therapeutic effects, in association with one or more suitable pharmaceutical excipients such as carriers. Methods for preparing such dosage forms are known or will be apparent to those skilled in the art. For example, in some embodiments, a chewing gum dosage form of the present invention can be prepared according to the procedures set forth in U.S. Pat. No. 4,405,647. In other embodiments, a tablet, lozenge, or candy dosage form of the present invention can be prepared according to the procedures set forth, for example, in *Remington: The Science and Practice of Pharmacy*, $20^{th}$ Ed., Lippincott, Williams & Wilkins (2003); *Pharmaceutical Dosage Forms, Volume 1: Tablets*, $2^{nd}$ Ed., Marcel Dekker, Inc., New York, N.Y. (1989); and similar publications. The dosage form to be administered will, in any event, contain a quantity of the therapeutic agent in a therapeutically effective amount for relief of the condition being treated when administered in accordance with the teachings of this invention.

As used herein, the term "carrier" refers to a typically inert substance used as a diluent or vehicle for a drug such as a therapeutic agent. The term also encompasses a typically inert substance that imparts cohesive qualities to the composition. Suitable carriers for use in the compositions of the present invention include, without limitation, a binder, a gum base, and combinations thereof. Non-limiting examples of binders include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. These binders can be pre-processed to improve their flowability and taste by methods known in the art such as freeze drying (see, e.g., Fundamentals of Freeze-Drying, *Pharm. Biotechnol.*, 14:281-360 (2002); Lyophililization of Unit Dose Pharmaceutical Dosage Forms, *Drug. Dev. Ind. Pharm.*, 29:595-602 (2003)); solid-solution preparation (see, e.g., U.S. Pat. No. 6,264,987); and lubricant dusting and wet-granulation preparation with a suitable lubricating agent (see, e.g., *Remington: The Science and Practice of Pharmacy*, supra). For example, Mannogem® and Sorbogem®, sold by SPI Pharma Group (New Castle, Del.), are freeze-dried processed forms of mannitol and sorbitol, respectively. Typically, the compositions of the present invention comprise from about 25% to about 90% by weight of the binder, and preferably from about 50% to about 80%. However, one skilled in the art will appreciate that the compositions of the present invention can be made without any binders, e.g., to produce a highly friable dosage form.

Non-limiting examples of gum bases include materials selected from among the many water-insoluble and saliva-insoluble gum base materials known in the art. For example, in some instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000). Typically, the gum base comprises from about 25% to about 75% by weight of these polymers, and preferably from about 30% to about 60%.

The compositions of the present invention can additionally include lubricating agents; wetting agents; emulsifying agents; solubilizing agents; suspending agents; preserving agents such as methyl-, ethyl-, and propyl-hydroxy-benzoates, butylated hydroxytoluene, and butylated hydroxyanisole; sweetening agents; flavoring agents; coloring agents; and disintegrating agents (i.e., dissolving agents) such as crospovidone as well as croscarmellose sodium and other cross-linked cellulose polymers.

Lubricating agents can be used to prevent adhesion of the dosage form to the surface of the dies and punches, and to reduce inter-particle friction. Lubricating agents may also facilitate ejection of the dosage form from the die cavity and improve the rate of granulation flow during processing. Examples of suitable lubricating agents include, without limitation, magnesium stearate, calcium stearate, zinc stearate, stearic acid, simethicone, silicon dioxide, talc, hydrogenated vegetable oil, polyethylene glycol, mineral oil, and combinations thereof. The compositions of the present invention can comprise from about 0% to about 10% by weight of the lubricating agent, and preferably from about 1% to about 5%.

Sweetening agents can be used to improve the palatability of the composition by masking any unpleasant tastes it may have. Examples of suitable sweetening agents include, without limitation, compounds selected from the saccharide family such as the mono-, di-, tri-, poly-, and oligosaccharides; sugars such as sucrose, glucose (corn syrup), dextrose, invert sugar, fructose, maltodextrin, and polydextrose; saccharin and salts thereof such as sodium and calcium salts; cyclamic acid and salts thereof; dipeptide sweeteners; chlorinated sugar derivatives such as sucralose and dihydrochalcone; sugar alcohols such as sorbitol, sorbitol syrup, mannitol, xylitol, hexa-resorcinol, and the like, and combinations thereof. Hydrogenated starch hydrolysate, and the potassium, calcium, and sodium salts of 3,6-dihydro-6-methyl-1-1,2,3-oxathiazin-4-one-2,2-dioxide may also be used. Of the foregoing, sorbitol, mannitol, and xylitol, either alone or in combination, are preferred sweetening agents. The compositions of the present invention can comprise from about 0% to about 80% by weight of the sweetening agent, preferably from about 5% to about 75%, and more preferably from about 25% to about 50%.

Flavoring agents can also be used to improve the palatability of the composition. Examples of suitable flavoring agents include, without limitation, natural and/or synthetic (i.e., artificial) compounds such as peppermint, spearmint, wintergreen, cinnamon, menthol, cherry, strawberry, watermelon, grape, banana, peach, pineapple, apricot, pear, raspberry, lemon, grapefruit, orange, plum, apple, fruit punch, passion fruit, chocolate (e.g., white, milk, dark), vanilla, caramel, coffee, hazelnut, combinations thereof, and the like. Coloring agents can be used to color code the composition, for example, to indicate the type and dosage of the therapeutic agent therein. Suitable coloring agents include, without limitation, natural and/or artificial compounds such as FD & C coloring agents, natural juice concentrates, pigments such as titanium oxide, silicon dioxide, and zinc oxide, combinations thereof, and the like. The compositions of the present invention can comprise from about 0% to about 10% by weight of the flavoring and/or coloring agent, preferably from about 0.1% to about 5%, and more preferably from about 2% to about 3%.

1. Chewing Gums

When the dosage form is a chewing gum, the compositions of the present invention comprise a hypnotic agent or a pharmaceutically acceptable salt thereof, a carrier such as a gum base, a binary or ternary buffer system, and optionally a protecting agent. The chewing gum composition may further comprise lubricating agents, wetting agents, emulsifying agents, solubilizing agents; suspending agents, preserving agents, sweetening agents, flavoring agents, and coloring agents. Typically, the chewing gum composition comprises from about 0.001% to about 10.0% by weight of the hypnotic agent (in whatever chosen form, measured as per its free base form), more typically from about 0.01% to about 5.0%, and still more typically from about 0.1% to about 3.0%. One skilled in the art understands that the foregoing percentages will vary depending upon the particular source of hypnotic agent utilized, the amount of hypnotic agent desired in the final formulation, as well as on the particular release rate of hypnotic agent desired. The binary or ternary buffer system of the chewing gum composition provides for a final salivary pH in excess of at least about 7.8, preferably at least about 8.5, and more preferably at least about 9 (e.g., about 9-11). The chewing gum composition typically comprises from about 20% to about 95% of the gum base, more typically from about 30% to about 85%, and most typically from about 50% to about 70% of the gum base.

The chewing gum composition may further comprise a protecting agent. The protecting agent coats at least part of the therapeutic agent, typically upon the mixing of the two agents. The protecting agent may be mixed with the therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the gum base so that the therapeutic agent may be more easily released from the gum base. In this way, the therapeutic agent may be delivered across the mucous membranes of the oral cavity within about 5 to about 20 minutes of chewing, preferably within about 10 minutes of chewing. A variety of different protecting agents may be used. Examples of suitable protecting agents include, without limitation, calcium stearate, glycerin monostearate, glyceryl behenate, glyceryl palmitostearate, hydrogenated castor oil, hydrogenated vegetable oil type I, light mineral oil, magnesium lauryl sulfate, magnesium stearate, mineral oil, poloxamer, polyethylene gycol, sodium benzoate, sodium chloride, sodium lauryl sulfate, stearic acid, cab-o-sil, talc, zinc stearate, and combinations thereof.

The gum base may additionally include plasticizers such as softeners or emulsifiers. Such plasticizers may, for example, help reduce the viscosity of the gum base to a desirable consistency and improve its overall texture and bite. Plasticizers may also facilitate the release of the therapeutic agent upon mastication. Non-limiting examples of plasticizers include lecithin, mono- and diglycerides, lanolin, stearic acid, sodium stearate, potassium stearate, glycerol triacetate, glycerol monostearate, glycerin, and combinations thereof. The gum base typically comprises from about 0% to about 20% by weight of the plasticizer, and more typically from about 5% to about 15%.

The gum base may further comprise waxes such as beeswax and microcrystalline wax, fats or oils such as soybean and cottonseed oil, and combinations thereof. Typically, the gum base comprises from about 0% to about 25% by weight of these waxes and oils, and more typically comprises from about 15% to about 20%.

In addition, the gum base may further comprise one or more elastomeric solvents such as rosins and resins. Non-limiting examples of such solvents include methyl, glycerol, and pentaerythritol esters of rosins, modified rosins such as hydrogenated, dimerized or polymerized rosins, or combinations thereof (e.g., pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin such as polymers of alpha-pinene or beta-pinene, terpene resins including polyterpene, and combinations thereof). Typically, the gum base comprises from about 0% to about 75% of the elastomeric solvent, and more typically less than about 10%.

The gum base may further comprise a filler material to enhance the chewability of the final chewing gum composition. Fillers that are substantially non-reactive with other components of the final chewing gum formulation are preferable. Examples of suitable fillers include, without limitation, calcium carbonate, magnesium silicate (i.e., talc), dicalcium phosphate, metallic mineral salts (e.g., alumina, aluminum hydroxide, and aluminum silicates), and combinations thereof. Typically, the gum base comprises from about 0% to about 30% by weight of the filler, and more typically from about 10% to about 20%.

One skilled in the art will appreciate that the gum base need not be prepared from its individual components. For example, the gum base can be purchased with the desired ingredients contained therein, and can be modified to include additional agents. Several manufacturers produce gum bases suitable for use with the described chewing gum compositions. Examples of such gum bases include, without limitation, Pharmagum™ M, S, or C (SPI Pharma Group; New Castle, Del.). In general, Pharmagum™ comprises a mixture of gum base, sweetening agent, plasticizer, and sugar.

In certain instances, the chewing gum composition includes a therapeutic agent centerfill. A centerfill may be particularly suitable when immediate release of the therapeutic agent is preferred. In addition, encapsulating the therapeutic agent in a centerfill may help to mask any undesirable taste that the therapeutic agent may have. In these instances, the gum base surrounds, at least in part, a centerfill. The centerfill comprises at least one therapeutic agent, and may be a liquid or semi-liquid material. The centerfill material can be a synthetic polymer, a semi-synthetic polymer, low-fat, or fat-free and contain one or more sweetening agents, flavoring agents, coloring agents, and/or scenting agents. Preferably, the centerfill includes a binary or ternary buffer system as described herein. Methods for preparing a centerfill chewing gum are described, for example, in U.S. Pat. No. 3,806,290, which is hereby incorporated by reference in its entirety.

The chewing gum compositions can have any desired shape, size, and texture. For example, the chewing gum can have the shape of a stick, tab, gumball, and the like. Similarly, the chewing gum can be any desirable color. For example, the chewing gum can be any shade of red, blue, green, orange, yellow, violet, indigo, and mixtures thereof, and can be color coded to indicate the type and dosage of the therapeutic agent therein. The chewing gum can be individually wrapped or grouped together in pieces for packaging by methods well known in the art.

2. Tablets

When the dosage form is a tablet such as a dissolving tablet (i.e., disintegrating tablet) or chewable tablet, the compositions of the present invention comprise a hypnotic agent or a pharmaceutically acceptable salt thereof, a carrier such as a binder, and a binary or ternary buffer system. The tablet composition may further comprise lubricating agents, wetting agents, emulsifying agents, solubilizing agents; suspending agents, preserving agents, sweetening agents, flavoring agents, coloring agents, and disintegrating agents. Typically, the tablet compositions of the present invention comprise from about 0.001% to about 10.0% by weight of the hypnotic agent (in whatever chosen form, measured as per its free base form), and more typically from about 1.0% to about 5.0%. In some embodiments, about 4.0% by weight of the hypnotic agent is used. One skilled in the art understands that the foregoing percentages will vary depending upon the particular source of hypnotic agent utilized, the amount of hypnotic agent desired in the final formulation, as well as on the particular release rate of hypnotic agent desired. The binary or ternary buffer system of the tablet composition provides for a final salivary pH in excess of at least about 7.8, preferably at least about 8.5, and more preferably at least about 9 (e.g., about 9-11).

In certain embodiments, the tablet is a dissolving tablet such as a slow-dissolving or quick-dissolving tablet that is dissolved by a subject's saliva, without the need for chewing. For example, a dissolving tablet placed on the subject's tongue can be used for buccal delivery of the therapeutic agent. Alternatively, a dissolving tablet placed underneath the subject's tongue can be used for sublingual delivery of the therapeutic agent. This type of dosage form may be particularly desirable for pediatric and geriatric patients, since small children and aged individuals often have difficulty chewing certain items. Typically, the dissolving tablet is formulated to dissolve within about 1 to about 15 minutes, preferably within about 2 to about 10 minutes, e.g., within about 2, 3, 4, 5, 6, 7, 8, 9, or 10 minutes, following administration. One skilled in the art will understand that quick-dissolving tablets dissolve faster than slow-dissolving tablets, which are typically dissolved gradually rather than rapidly by a subject's saliva. In a preferred embodiment, the slow-dissolving or quick-dissolving tablet delivers the therapeutic agent across the sublingual mucosa.

In certain other embodiments, the tablet is a chewable tablet that is chewed by a subject and formulated to dissolve either rapidly or gradually. For example, a chewable tablet placed on the subject's tongue can be used for buccal delivery of the therapeutic agent. During chewing, the chewable tablet can be moved around within the mouth and can sometimes be parked between the gums and the cheeks or underneath the tongue. As a result, at least a portion of the therapeutic agent contained within a chewable tablet may also be delivered sublingually (i.e., across the sublingual mucosa). Typically, the chewable tablet is formulated to dissolve within about 1 to about 15 minutes, preferably within about 2 to about 10 minutes, e.g., within about 2, 3, 4, 5, 6, 7, 8, 9, or 10 minutes, following administration.

As described above, the dissolving and chewable tablets of the present invention are typically formulated to dissolve within about 1 to 15 minutes following administration. However, while these time frames are amenable to maximum exposure of the therapeutic agent to the oral mucosa (e.g., to the sublingual and/or buccal mucosa), they are not always amenable to user compliance (e.g., users may swallow too frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the tablet size (e.g., from about 700-800 mg to about 200-300 mg) without reducing the concentration or amount per unit dose of the buffer system or the therapeutic agent. In addition, subtle changes to the tablet formulation such as, for example, replacing one flavoring agent for another (e.g., chocolate for spearmint) or replacing one binder or sweetening agent for another (e.g., lactose for mannitol or sorbitol) may be used to reduce salivation.

The carrier present in the tablets of the present invention is typically a binder that is useful in keeping the tablet in a semi-solid state, and may be a solid or a liquid, and may for example be a high-melting point fat or waxy material. Materials suitable as binders are discussed in detail above and may be used alone or in combination in the tablet compositions of the present invention. In addition, binders such as mannitol, sorbitol, lactose, sucrose, and inositol can impart properties to the tablet that permit or enhance its disintegration in the mouth.

The tablet composition may further comprise a protecting agent. The protecting agent coats at least part of the therapeutic agent, typically upon the mixing of the two agents. The protecting agent may be mixed with the therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the binder so that the therapeutic agent may be more easily released from the binder. In this way, the therapeutic agent may be delivered across the mucous membranes of the oral cavity within about 5 to about 20 minutes, preferably within about 10 minutes. Materials suitable as protecting agents are discussed in detail above and may be used alone or in combination in the tablet compositions of the present invention.

The tablet composition may also comprise one or more elastomeric solvents such as rosins and resins. Non-limiting examples of such solvents are discussed in detail above and may be used alone or in combination in the tablet compositions of the present invention. In addition, the tablet composition may further comprise waxes such as beeswax and microcrystalline wax, fats or oils such as soybean and cottonseed oil, and combinations thereof. Moreover, the tablet composition may additionally include plasticizers such as softeners or emulsifiers. Such plasticizers may, for example, help reduce the viscosity of the salivary solution of the dissolved tablet to a desirable consistency and improve its overall texture and bite and help facilitate the release of the therapeutic agent. Non-limiting examples of such plasticizers are discussed in detail above and may be used alone or in combination in the tablet compositions of the present invention.

In certain instances, the tablet composition includes a therapeutic agent centerfill. A centerfill may be particularly suitable when immediate release of the therapeutic agent is preferred. In addition, encapsulating the therapeutic agent in a centerfill may help to mask any undesirable taste that the therapeutic agent may have. In these instances, the binder surrounds, at least in part, a centerfill. The centerfill comprises at least one therapeutic agent, and may be a liquid or semi-liquid material. The centerfill material can be a synthetic polymer, a semi-synthetic polymer, low-fat, or fat-free and contain one or more sweetening agents, flavoring agents, coloring agents, and/or scenting agents. Preferably, the centerfill includes a binary or ternary buffer system as described herein.

In certain other instances, the tablet composition of the present invention is multilayered. In this way, the dissolving or chewable tablet can be designed to provide more than one therapeutic agent, e.g., two or more hypnotic agents or one or more hypnotic agents in combination with one or more non-hypnotic therapeutic agents. For example, with a bi-layered tablet, the first layer contains a hypnotic agent and the second layer contains the same or different hypnotic agent or a non-hypnotic therapeutic agent. Typically, the first layer comprises the dissolving or chewable portion of the tablet, and the second (i.e., subsequent) layer is coated by the first layer. This type of formulation may be particularly suitable when immediate release of the hypnotic agent, followed by gastrointestinal absorption of a second therapeutic agent, is desirable. Gastrointestinal absorption of the second therapeutic agent may be desirable, for example, in order to mitigate co-morbid symptoms or to sustain the therapeutic benefit of the hypnotic agent in the dissolving or the chewable portion of the tablet. Alternatively, the second layer is present as a layer lateral to the first layer. The second layer typically comprises at least one therapeutic agent, and can also comprise one or more sweetening agents, flavoring agents, coloring agents, and scenting agents as described above. In some instances, the second layer further includes a binary or ternary buffer system as described herein.

In still other instances, the combination of hypnotic agents with or without non-hypnotic therapeutic agents need not take the form of a multilayered tablet, but instead comprises a single homogenous tablet layer. This type of formulation may also be used in the case where gastrointestinal absorption of at least one therapeutic agent is desirable. In this case, the relative extent of ionization of the two or more therapeutic agents determines how they are to be absorbed. For example, those therapeutic agents that are un-ionized are absorbed through the oral mucosa, while the ionized agents are swallowed for gastrointestinal absorption.

The tablet compositions can have any desired shape, size, and texture. For example, the tablet can have the shape of a stick, tab, pellet, sphere, and the like. Similarly, the tablet can be any desirable color. For example, the tablet can be any shade of red, blue, green, orange, yellow, violet, indigo, and mixtures thereof, and can be color coded to indicate the type and dosage of the therapeutic agent therein. The tablets can be individually wrapped or grouped together in pieces for packaging by methods well known in the art.

3. Lozenges

When the dosage form is a lozenge or candy, the compositions of the present invention comprise a hypnotic agent or a pharmaceutically acceptable salt thereof, a carrier such as a binder, and a binary or ternary buffer system. The lozenge or candy composition may further comprise lubricating agents, wetting agents, emulsifying agents, solubilizing agents; suspending agents, preserving agents, sweetening agents, flavoring agents, coloring agents, and disintegrating agents. A general discussion of lozenges and candies is provided, e.g., in *Pharmaceutical Dosage Forms, Volume* 1: *Tablets, 2$^{nd}$ Ed.*, Marcel Dekker, Inc., New York, N.Y., pages 75-418 (1989). Typically, the lozenge compositions of the present invention comprise from about 0.001% to about 10.0% by weight of the hypnotic agent (in whatever chosen form, measured as per its free base form), and more typically from about 1.0% to about 5.0%. In some embodiments, about 4.5% by weight of the hypnotic agent is used. One skilled in the art understands that the foregoing percentages will vary depending upon the particular source of hypnotic agent utilized, the amount of hypnotic agent desired in the final formulation, as well as on the particular release rate of hypnotic agent desired. The binary or ternary buffer system of the lozenge composition provides for a final salivary pH in excess of at least about 7.8, preferably at least about 8.5, and more preferably at least about 9 (e.g., about 9-11).

In certain embodiments, the lozenge or candy is dissolved by a subject's saliva, without the need for chewing. For example, a lozenge placed on the subject's tongue can be used for buccal delivery of the therapeutic agent. Alternatively, a lozenge placed underneath the subject's tongue can be used for sublingual delivery of the therapeutic agent. This type of dosage form may be particularly desirable for pediatric and geriatric patients, since small children and aged individuals often have difficulty chewing certain items. Typically, the lozenge is formulated to dissolve within about 1 to about 15 minutes, preferably within about 2 to about 10 minutes, e.g., within about 2, 3, 4, 5, 6, 7, 8, 9, or 10 minutes, following administration. In a preferred embodiment, the lozenge or candy delivers the therapeutic agent across the sublingual mucosa.

As described above, the lozenges the present invention are typically formulated to dissolve within about 1 to 15 minutes following administration. However, while these time frames are amenable to maximum exposure of the therapeutic agent to the oral mucosa (e.g., to the sublingual and/or buccal mucosa), they are not always amenable to user compliance (e.g., users may swallow too frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the lozenge size (e.g., from about 700-800 mg to about 200-300 mg) without reducing the concentration or amount per unit dose of the buffer system or the therapeutic agent. In addition, subtle changes to the lozenge formulation such as, for example, replacing one flavoring agent for another (e.g., chocolate for spearmint) or replacing one binder or sweetening agent for another (e.g., lactose for mannitol or sorbitol) may be used to reduce salivation.

The carrier present in the lozenges of the present invention is typically a binder that is useful in keeping the lozenge in a semi-solid state, and may be a solid or a liquid, and may for example be a high-melting point fat or waxy material. Materials suitable as binders are discussed in detail above and may be used alone or in combination in the lozenge compositions of the present invention. In addition, binders such as mannitol, sorbitol, lactose, sucrose, and inositol can impart properties to the lozenge that permit or enhance its disintegration in the mouth.

The lozenge composition may further comprise a protecting agent. The protecting agent coats at least part of the therapeutic agent, typically upon the mixing of the two agents. The protecting agent may be mixed with the therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the binder so that the therapeutic agent may be more easily released from the binder. In this way, the therapeutic agent may be delivered across the mucous membranes of the oral cavity within about 5 to about 20 minutes, preferably within about 10 minutes. Materials suitable as protecting agents are discussed in detail above and may be used alone or in combination in the lozenge compositions of the present invention.

The lozenge composition may also comprise one or more elastomeric solvents such as rosins and resins. Non-limiting examples of such solvents are discussed in detail above and may be used alone or in combination in the tablet compositions of the present invention. In addition, the lozenge composition may further comprise waxes such as beeswax and microcrystalline wax, fats or oils such as soybean and cottonseed oil, and combinations thereof. Moreover, the lozenge composition may additionally include plasticizers such as softeners or emulsifiers. Such plasticizers may, for example, help reduce the viscosity of the salivary solution of the dissolved lozenge to a desirable consistency and improve its overall texture and bite and help facilitate the release of the therapeutic agent. Non-limiting examples of such plasticizers are discussed in detail above and may be used alone or in combination in the lozenge compositions of the present invention.

In certain instances, the lozenge composition includes a therapeutic agent centerfill. A centerfill may be particularly suitable when immediate release of the therapeutic agent is preferred. In addition, encapsulating the therapeutic agent in a centerfill may help to mask any undesirable taste that the therapeutic agent may have. In these instances, the binder surrounds, at least in part, a centerfill. The centerfill comprises at least one therapeutic agent, and may be a liquid or semi-liquid material. The centerfill material can be low-fat or fat free and contain one or more sweetening agents, flavoring agents, coloring agents, and/or scenting agents. Preferably, the centerfill includes a binary or ternary buffer system as described herein.

In certain other instances, the lozenge composition of the present invention is multilayered. In this way, the lozenge can be designed to provide more than one therapeutic agent, e.g., two or more hypnotic agents or one or more hypnotic agents in combination with one or more non-hypnotic therapeutic agents. For example, with a bi-layered lozenge, the first layer contains a hypnotic agent and the second layer contains the same or different hypnotic agent or a non-hypnotic therapeutic agent. Typically, the first layer comprises the dissolving portion of the lozenge, and the second (i.e., subsequent) layer is coated by the first layer. This type of formulation may be particularly suitable when immediate release of the hypnotic agent, followed by gastrointestinal absorption of a second therapeutic agent, is desirable. Gastrointestinal absorption of the second therapeutic agent may be desirable, for example, in order to mitigate co-morbid symptoms or to sustain the therapeutic benefit of the hypnotic agent in the dissolving portion of the lozenge. Alternatively, the second layer is present as a layer lateral to the first layer. The second layer typically comprises at least one therapeutic agent, and can also comprise one or more sweetening agents, flavoring agents, coloring agents, and scenting agents as described above. In some instances, the second layer further includes a binary or ternary buffer system as described herein.

In still other instances, the combination of hypnotic agents with or without non-hypnotic therapeutic agents need not take the form of a multilayered lozenge, but instead comprises a single homogenous lozenge layer. This type of formulation may also be used in the case where gastrointestinal absorption of at least one therapeutic agent is desirable. In this case, the relative extent of ionization of the two or more therapeutic agents determines how they are to be absorbed. For example, those therapeutic agents that are un-ionized are absorbed through the oral mucosa, while the ionized agents are swallowed for gastrointestinal absorption.

The lozenge compositions can have any desired shape, size, and texture. For example, the lozenge can have the shape of a stick, tab, pellet, sphere, and the like. Similarly, the lozenge can be any desirable color. For example, the lozenge can be any shade of red, blue, green, orange, yellow, violet, indigo, and mixtures thereof, and can be color coded to indicate the type and dosage of the therapeutic agent therein. The lozenges can be individually wrapped or grouped together in pieces for packaging by methods well known in the art.

D. Methods of Administration

The compositions of the present invention are useful in therapeutic applications, e.g., for treating a sleep disorder. Importantly, the compositions of the present invention provide the rapid and predictable delivery of a hypnotic agent across the oral mucosa with surprisingly low inter-subject variability in terms of maximum plasma concentration ($C_{max}$) and the time to reach the maximum plasma concentration ($T_{max}$) by raising the pH of saliva to a pH greater than about 7.8, irrespective of the starting pH of saliva. In particular, the delivery of the therapeutic agent across the oral mucosa avoids hepatic first pass metabolism, degradation within the gastrointestinal tract, and drug loss during absorption. As a result, the therapeutic agent reaches the systemic circulation in a substantially shorter period of time and at a substantially higher concentration than with traditional oral (e.g., tablet) administration.

In addition, the compositions of the present invention offer advantages over compositions for oral mucosal administration that do not contain the buffer system described herein. In particular, because the buffer system in the compositions of the present invention helps convert substantially all of the therapeutic agent from its ionized form to its un-ionized form, the therapeutic agent reaches the systemic circulation in a substantially shorter period of time (e.g., reducing the time to onset of therapeutic activity) and at a substantially higher concentration than with compositions for oral mucosal administration that do not contain the buffer system.

The compositions of the present invention have particular utility in the area of human and veterinary therapeutics. Generally, administered dosages will be effective to deliver picomolar to micromolar concentrations of the hypnotic agent to the appropriate site.

Administration of the compositions of the present invention is preferably carried out via any of the accepted modes of administration to the mucous membranes of the oral cavity. Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. These regions differ from each other with respect to their anatomy, drug permeability, and physiological response to drugs. Preferably, the compositions of the present invention are administered to the sublingual mucosa, buccal mucosa, or a combination thereof.

The oral mucosa, possessing a rich blood supply and suitable drug permeability, is an especially attractive route of administration for systemic drug delivery. Furthermore, delivery of a therapeutic agent across the oral mucosa bypasses hepatic first pass metabolism, avoids enzymatic degradation within the gastrointestinal tract, and provides a more suitable enzymatic flora for drug absorption. As used herein, the term "sublingual delivery" refers to the administration of a therapeutic agent across the mucous membranes lining the floor of the mouth and/or the ventral tongue. The term "buccal delivery" as used herein refers to the administration of a therapeutic agent across the mucous membranes lining the cheeks.

The oral mucosa is composed of an outermost layer of stratified squamous epithelium. Beneath this layer lies a basement membrane, i.e., the lamina propria, followed by the submucosa as the innermost layer. The epithelium of the oral mucosa is similar to the stratified squamous epithelia found in the rest of the body in that it contains a mitotically active basal cell layer, advancing through a number of differentiating intermediate layers to the superficial layers, where cells are shed from the surface of the epithelium (Gandhi et al., *Ind. J Pharm. Sci.*, 50:145-152 (1988)). For example, the epithelium of the buccal mucosa is about 40-50 cell layers thick, while that of the sublingual epithelium contains somewhat fewer cell layers. The epithelial cells increase in size and become flatter as they travel from the basal layers to the superficial layers.

The turnover time for buccal mucosal epithelium, estimated at 5-6 days, is representative of the turnover time for sublingual mucosal epithelium as well as other epithelia in the oral mucosa (Harris et al., *J Pharm. Sci.*, 81:1-10 (1992)). The thickness of the oral mucosa varies depending on the site in the oral cavity. For example, the buccal mucosa measures at about 500-800 µm in thickness, while the hard and soft palatal mucosa, the sublingual mucosa, the ventral tongue, and the gingival mucosa measure at about 100-200 µm in thickness. The composition of the epithelium also varies depending on the site in the oral cavity. For example, the mucosae of areas subject to mechanical stress (i.e., the gingivae and hard palate) are keratinized similar to the epidermis. However, the mucosae of the soft palate, the sublingual region, and the buccal region are not keratinized (Harris et al., supra). The keratinized epithelia contain neutral lipids like ceramides and acylceramides, which have been associated with providing a barrier function. As a result, these epithelia are relatively impermeable to water. In contrast, non-keratinized epithelia, such as sublingual and buccal epithelia, do not contain acylceramides and have only small amounts of ceramide (Wertz et al., *Crit. Rev. Ther. Drug Carr. Sys.*, 8:237-269 (1991); Squier et al., *J. Invest. Dermat.*, 96:123-126 (1991); Squier et al., in

*Oral Mucosal Drug Delivery*, Ed. M. J. Rathbone, Marcel Dekker, Inc., New York, N.Y., 1-26 (1996)). Non-keratinized epithelia also contain small amounts of neutral but polar lipids, e.g., cholesterol sulfate and glucosyl ceramides. As such, these epithelia have been found to be considerably more permeable to water than keratinized epithelia (Harris et al, supra; Wertz et al., supra; Squier et al., supra, 1991).

In general, the oral mucosa is a somewhat leaky epithelia intermediate between that of the epidermis and intestinal mucosa. For example, the permeability of the buccal mucosa is estimated to be about 4-4000 times greater than that of skin (Galey et al., *J. Invest. Dermat.*, 67:713-717 (1976)). The permeability of different regions of the oral mucosa generally decrease in the order of sublingual mucosa greater than buccal mucosa, and buccal mucosa greater than palatal mucosa (Harris et al., supra). This permeability is generally based upon the relative thickness and degree of keratinization of these membranes, with the sublingual mucosa being relatively thin and non-keratinized, the buccal mucosa being thicker and non-keratinized, and the palatal mucosa being intermediate in thickness, but keratinized.

The epithelial cells of the oral mucosa are surrounded by mucus comprising primarily complexes of proteins and carbohydrates that may or may not be attached to certain regions on the cell surface. The mucus may play a role in cell-cell adhesion, as well as acting as a lubricant, allowing cells to move relative to one another (Tabak et al., *J. Oral Pathol.*, 11:1-17 (1982)). In stratified squamous epithelia found elsewhere in the body, mucus is synthesized by specialized mucus secreting cells such as goblet cells; however, in the oral mucosa, mucus is secreted by the major and minor salivary glands as part of saliva (Tabak et al., supra; Rathbone et al., *Adv. Drug Del. Rev.*, 13:1-22 (1994)). At physiological pH, the mucus network carries a negative charge due to the sialic acid and sulfate residues present on the carbohydrates. At this pH, mucus can form a strongly cohesive gel structure that binds to the epithelial cell surface as a gelatinous layer (Gandhi et al., supra). Without being bound to any particular theory, the buffer systems of the present invention neutralize the sialic acid residues present on the carbohydrates and prevent them from interacting with the therapeutic agent, thereby further enhancing drug permeation.

Another feature of the environment of the oral cavity is the presence of saliva produced by the salivary glands. Saliva is the protective fluid for all tissues of the oral cavity. Saliva is an aqueous fluid with about 1% organic and inorganic materials. The major determinant of the salivary composition is the flow rate, which in turn depends upon factors such as the time of day, the type of stimulus, and the degree of stimulation. The salivary pH typically ranges from about 5.5 to about 7.0, depending on the flow rate. For example, at high flow rates, the sodium and bicarbonate concentrations increase, leading to an increase in the pH. Because the daily salivary volume is between about 0.5 to about 2 liters, the oral cavity provides an aqueous environment for the hydration and/or dissolution of the oral mucosal dosage forms of the present invention.

The sublingual mucosa is the most highly permeable region of the oral cavity, and provides rapid absorption and high bioavailability of a drug in a convenient, accessible, and well-accepted route of administration (Harris et al., supra). Suitable sublingual dosage forms include, without limitation, tablets (e.g., quick-dissolving, slow-dissolving), lozenges, candy, and soft gelatin capsules filled with liquid drug. Such systems create a very high drug concentration in the sublingual region before they are systemically absorbed across the sublingual mucosa. As a result, the sublingual mucosa is particularly well-suited for producing a rapid onset of action, and sublingual dosage forms can be used to deliver drugs with shorter delivery period requirements and/or less frequent dosing regimens. Although the buccal mucosa is considerably less permeable than the sublingual area, rapid absorption and high bioavailability of a drug can also be observed with buccal administration. Suitable buccal dosage forms include, without limitation, chewing gums, tablets (e.g., quick-dissolving, slow-dissolving), lozenges, candy, and the like. Both the buccal mucosa and the sublingual mucosa are far superior to the gastrointestinal tract for providing increased absorption and bioavailability of a drug.

To increase the permeability of drugs through the oral mucosa, penetration enhancers can be included in the dosage forms of the present invention. The penetration enhancers may be of the type that alters the nature of the oral mucosa to enhance penetration, or of the type that alters the nature of the therapeutic agent to enhance penetration through the oral mucosa. Suitable penetration enhancers include, without limitation, polyoxyethylene 23-lauryl ether, aprotin, azone, benzalkonium chloride, cetylpyridinium chloride, cetyltrimethylammonium bromide, cyclodextrin, dextran sulfate, lauric acid, propylene glycol, lysophosphatidylcholine, menthol, methoxysalicylate, methyloleate, oleic acid, phosphatidylcholine, polyoxyethylene, polysorbate 80, sodium ethylenediaminetetraacetic acid ("EDTA"), sodium deoxycholate, sodium glycocholate, sodium glycodeoxycholate, sodium lauryl suflate, sodium salicylate, sodium taurocholate, sodium taurodeoxycholate, as well as certain sulfoxides and glycosides, and combinations thereof.

IV. Examples

The following examples are offered to illustrate, but not to limit, the claimed invention.

Example 1

Zolpidem Membrane Assay

This example illustrates the beneficial effects of pH adjustment on membrane penetration for a zolpidem dosage form.

The effect of pH adjustment on the extent of ionization, and hence, the extent to which a therapeutic agent will traverse the mucous membrane can be demonstrated using a membrane assay; see, e.g., Kansy et al., *J. Med. Chem.*, 41:1007-1010 (1998); and Avdeef, *Curr. Topics Med. Chem.*, 1:277-351 (2001). This assay uses a lipid-coated membrane to predict lipid mucosal membrane penetration. The membrane apparatus consists of a dodecane membrane sandwiched between a donor and acceptor cell. The lipid-coated membrane is less porous then the mucous membrane of the oral cavity. Thus, the enhancement seen in the membrane assay is very likely to be magnified in vivo.

Membrane assays were performed using zolpidem tartrate solutions at a pH of 5.8, 6.8, and 7.8. The alkaline pH values of 7.8 were adjusted using freshly prepared 0.01 M sodium bicarbonate/sodium carbonate buffer solution. The acidic pH of 5.8 was achieved using a 0.01 M acetate buffer solution (a mixture of sodium acetate and acetic acid). The neutral pH of 6.8 was achieved by adding 0.01 M acetate solution to the sodium bicarbonate/sodium carbonate buffer solution. Permeation through the membrane was measured by determining the concentration of zolpidem in the acceptor cell and is expressed as $P_e$ (effective permeability in centimeters per second). As shown in Table 1 below, the effective permeability of zolpidem increased by more than 53% at a pH of 7.8 relative to a pH of 6.8 and 129% relative to a pH of 5.8. FIG.

1 shows a bar chart illustrating the relationship between pH and zolpidem membrane permeability.

TABLE 1

Effective permeability ($P_e$) of zolpidem in a membrane assay.

| pH | $p_e$ (cm/s) |
|---|---|
| 5.8 | 19.8 |
| 6.8 | 29.6 |
| 7.8 | 45.3 |

Example 2

Zolpidem Gum Compositions

This example illustrates the zolpidem chewing gum compositions of the present invention.

Zolpidem can be formulated as a chewing gum composition as described above. In these embodiments, the unit dose or serving of the chewing gum comprises from about 0.1 to about 100 milligrams (mg) zolpidem (as measured in its tartrate salt form), preferably from about 1 to about 50 mg, and more preferably from about 2 to about 25 mg. In other embodiments, the unit dose comprises from about 2 to about 20 mg zolpidem, preferably from about 5 to about 15 mg. Extra zolpidem, for example, up to from about 10% to about 25% by weight, can be added as "overage" or as the amount that may be expected to be "washed away" and not otherwise released or absorbed during mastication.

In another embodiment, the unit dose or serving of the chewing gum comprises from about 0.81 to about 42 mg zolpidem in its base form, and more preferably from about 1.64 to about 20.5 mg. In other embodiments, the unit dose comprises from about 1.64 to about 16.4 mg zolpidem in its free base form, preferably from about 1.64 to about 12.3 mg, and more preferably from about 1.64 to about 8.2 mg, e.g., about 1.64, 2.46, 3.28, 4.1, 4.92, 5.78, 6.56, 7.38, or 8.2 mg. In additional embodiments, the unit dose comprises a mixture of zolpidem in free base form and salt form (e.g., zolpidem tartrate).

Given in weight percentages, the zolpidem chewing gum composition comprises from about 0.001% to about 10.0% zolpidem (in whatever chosen form, measured as per its free base form), preferably from about 0.05% to about 2.0%, and more preferably from about 0.1% to about 1.0%. In some embodiments, about 0.25% zolpidem is used. One skilled in the art understands that the foregoing percentages will vary depending upon the particular source of zolpidem utilized, the amount of zolpidem desired in the final formulation, as well as on the particular release rate of zolpidem desired. The buffer system of the zolpidem chewing gum composition provides for a final salivary pH in excess of at least about 7.8, preferably at least about 8.5, and more preferably at least about 9 (e.g., about 9-11).

A zolpidem chewing gum was made according to the following procedure. Silicon dioxide USP (0.35 kg) was passed through a #20 mesh screen, and then loaded into a blender containing 0.810 kg mannitol granular USP and 9.569 kg Pharmagum™ C. The material was blended for 10 minutes. Zolpidem tartrate EP (0.034 kg) was ground with the silicon dioxide (0.02 kg) using a mortar and pestle. The remaining silicon dioxide, along with 0.228 kg magnesium stearate, was added into the mortar while continuing to grind. The ground materials were transferred into a plastic bag, and the mortar was rinsed using 0.01 kg silicone dioxide, and transferred into the bag. The contents of the bag were then blended for five minutes.

Equal parts of the blended bag contents and the blended mannitol gum base mixture were blended for an additional five minutes. This process was repeated until all the zolpidem and gum base mixture had been blended together. Sodium carbonate (0.110 kg), sodium bicarbonate (0.570 kg), gum acacia (0.43 kg), xanthan gum (0.013 kg), and aspartame (0.072 kg) were then loaded into the blender along with natural and artificial flavors and blended for ten minutes with 0.090 kg of silicon dioxide. The flavors used were as follows: natural and artificial grape flavor S.D. (0.215 kg), natural and artificial cherry flavor (0.108 kg), natural and artificial fruit punch flavor S.D. (0.180 kg), natural cherry WONF DURAROME® flavor (0.215 kg), and natural passion fruit type DURAROME® flavor (0.035 kg).

The blend was passed through a #12 mesh screen and then blended for an additional 15 minutes. Magnesium stearate (0.114 kg) was passed through a #20 mesh screen and added to the blend and blended for five minutes. The blend was collected and placed in plastic bags. Two silica gel desiccant bags were placed around the plastic bags to absorb ambient moisture. The blend was then compressed into tablets. By using the above-described procedure, the average particle size of the drug (i.e., zolpidem) in the chewing gum is about 20 microns, as compared to a typical average drug particle size of from about 75 to about 100 microns. In addition, the average particle size of the drug in the chewing gum is less than or equal to the average particle size of the carrier ingredients (e.g., gum base, binders, etc.).

The zolpidem chewing gum composition of the present invention can be used, e.g., for treatment of insomnia; see, Holm et al., *Drugs*, 59:865-889 (2000). In certain instances, after the introduction of a serving size piece of the chewing gum composition into the mouth, the subject chews the chewing gum as is normally done with any non-medicated type of chewing gum for about 5 to about 20 minutes, at approximately an average rate of about 10 to about 45 chews per minute. The gum is then discarded.

A typical dosage form of the zolpidem chewing gum of the present invention is designed to produce an average plasma concentration of at least from about 20 to about 300 nanograms of zolpidem per milliliter of plasma. For example, a 5 mg zolpidem chewing gum can be designed to produce a mean peak plasma concentration within the range of from about 20 to about 100 nanograms of zolpidem per milliliter of plasma within about 5 minutes to about 2 hours. Similarly, a 10 mg zolpidem chewing gum can be designed to produce a mean peak plasma concentration within the range of from about 100 to about 300 nanograms of zolpidem per milliliter of plasma within about 5 minutes to about 2 hours.

The chewing gum compositions of the present invention provide a convenient, reliable, practical, and painless system for delivering zolpidem across the oral mucosa. Notably, the chewing gum compositions are capable of rapidly delivering zolpidem with low inter-subject variability in terms of maximum plasma concentration ($C_{max}$) and the time to reach the maximum plasma concentration ($T_{max}$) so that a therapeutically effective amount of zolpidem enters the bloodstream within about 30 minutes, 20 minutes, 15 minutes, 10 minutes, 5 minutes, or even within about 1-2 minutes after zolpidem is released from the carrier.

Example 3

Zolpidem Tablet Compositions

This example illustrates the slow-dissolving, quick-dissolving, and chewable zolpidem tablet compositions of the present invention.

Zolpidem can be formulated as a tablet composition as described above. In these embodiments, the unit dose or serving of the tablet comprises from about 0.1 to about 100 milligrams (mg) zolpidem (as measured in its tartrate salt form), preferably from about 1 to about 50 mg, and more preferably from about 2 to about 25 mg. In other embodiments, the unit dose comprises from about 2 to about 20 mg zolpidem, preferably from about 2 to about 15 mg, and more preferably from about 2 to about 10 mg, e.g., about 2, 3, 4, 5, 6, 7, 8, 9, or 10 mg. In particularly preferred embodiments, the unit dose comprises a dose of zolpidem that is less than the dose typically used in commercial oral tablets, but possesses comparable or greater bioavailability and onset of therapeutic activity as well as lower variability of drug absorption. In such embodiments, unit doses of from about 2 to about 5 mg zolpidem are preferred, with unit doses of about 4 mg zolpidem being particularly preferred. Extra zolpidem, for example, up to from about 10% to about 25% by weight, can be added as "overage" or as the amount that may be expected to be "washed away" and not otherwise released or absorbed during tablet dissolution and/or mastication.

In another embodiment, the unit dose or serving of the tablet comprises from about 0.81 to about 42 mg zolpidem in its base form, and more preferably from about 1.64 to about 20.5 mg. In other embodiments, the unit dose comprises from about 1.64 to about 16.4 mg zolpidem in its free base form, preferably from about 1.64 to about 12.3 mg, and more preferably from about 1.64 to about 8.2 mg, e.g., about 1.64, 2.46, 3.28, 4.1, 4.92, 5.78, 6.56, 7.38, or 8.2 mg. In additional embodiments, the unit dose comprises a mixture of zolpidem in free base form and salt form (e.g., zolpidem tartrate).

Given in weight percentages, the zolpidem tablet composition comprises from about 0.001% to about 10.0% zolpidem (in whatever chosen form, measured as per its free base form), preferably from about 0.1% to about 8.0%, more preferably from about 1.0% to about 7.0%, and still more preferably from about 1.0% to about 5.0%. In some embodiments, about 4.0% zolpidem is used. One skilled in the art understands that the foregoing percentages will vary depending upon the particular source of zolpidem utilized, the amount of zolpidem desired in the final formulation, as well as on the particular release rate of zolpidem desired. The buffer system of the zolpidem tablet composition provides for a final salivary pH in excess of at least about 7.8, preferably at least about 8.5, and more preferably at least about 9 (e.g., about 9-11).

Zolpidem Slow-dissolving Tablets:

A zolpidem slow-dissolving tablet was made according to the following procedure. Magnesium stearate USP (0.35 kg) was passed through a #20 mesh screen, and then loaded into a blender containing 0.810 kg mannitol granular USP and 9.569 kg sorbitol. The material was blended for 10 minutes. Zolpidem tartrate EP (0.034 kg) was ground with the magnesium stearate (0.02 kg) using a mortar and pestle. The remaining silicon dioxide, along with 0.228 kg magnesium stearate was added into the mortar while continuing to grind. The ground materials were transferred into a plastic bag, and the mortar was rinsed using 0.01 kg silicone dioxide, and transferred into the bag. The contents of the bag were then blended for five minutes.

Equal parts of the blended bag contents and the blended mannitol mixture were blended for an additional five minutes. This process was repeated until all the zolpidem and mannitol mixture had been blended together. Sodium carbonate (0.110 kg), sodium bicarbonate (0.570 kg), gum acacia (0.43 kg), xanthan gum (0.013 kg), and aspartame (0.072 kg) were then loaded into the blender with natural and artificial flavors and blended for ten minutes with 0.090 kg of silicon dioxide. The flavors used were as follows: natural and artificial grape flavor S.D. (0.215 kg), natural and artificial cherry flavor (0.108 kg), natural and artificial fruit punch flavor S.D. (0.180 kg), natural cherry WONF DURAROME® flavor (0.215 kg), and natural passion fruit type DURAROME® flavor (0.035 kg).

The blend was passed through a #12 mesh screen and then blended for an additional 15 minutes. Magnesium stearate (0.114 kg) was passed through a #20 mesh screen and added to the blend and blended for five minutes. The blend was collected and placed in plastic bags. Two silica gel desiccant bags were placed around the plastic bags to absorb ambient moisture. The blend was then compressed into tablets. By using this procedure, the average particle size of the drug (i.e., zolpidem) in the slow-dissolving tablet is about 20 microns, as compared to a typical average drug particle size of from about 75 to about 100 microns. In addition, the average particle size of the drug in the slow-dissolving tablet is less than or equal to the average particle size of the carrier ingredients (e.g., gum base, binders, etc.).

A second zolpidem slow-dissolving tablet was made according to the formulation shown in Table 2 and the following procedure. Three separate blends of silicon dioxide with zolpidem, sodium bicarbonate, and sodium carbonate; mannitol and sorbitol; and spearmint flavor, sucralose, stearic acid, and magnesium stearate were prepared. The three blends were screened separately and mixed to form a single blend. The single blend was then compressed into tablets after testing for content uniformity. By using this procedure, the average particle size of the drug (i.e., zolpidem) in the slow-dissolving tablet is about 20 microns, which is less than or equal to the average particle size of the carrier ingredients (e.g., gum base, binders, etc.). The unit weight for each tablet was 250 mg. The pH of the tablet was about 9.8 and remained stable. These tablets dissolve within about 10 minutes following sublingual administration.

TABLE 2

Zolpidem slow-dissolving tablet formulation.

| Material | Unit Quantity (mg) | Batch Quantity (g) |
|---|---|---|
| Sodium Carbonate, NF | 17.000 | 357.000 |
| Sodium Bicarbonate USP | 23.000 | 483.000 |
| Zolpidem Tartrate, EP | 10.000 | 210.000 |
| Mannitol, USP | 40.000 | 840.000 |
| Sorbitol, NF | 136.000 | 2856.000 |
| Natural & Artificial Spearmint Flavor | 6.500 | 136.500 |
| Sucralose, NF | 1.000 | 21.000 |
| Silicon Dioxide, USP | 5.500 | 115.500 |
| Stearic Acid, NF | 3.500 | 73.500 |
| Magnesium Stearate, NF | 7.500 | 157.500 |

The batch quantity formulation produces 21,000 unit doses.

Zolpidem Quick-dissolving Tablets:

A zolpidem quick-dissolving tablet was made according to the following procedure. Mannitol (3.633 kg) and sorbitol (0.469 kg) were blended for ten minutes. Sodium carbonate (0.330 kg), sodium bicarbonate (0.165 kg), natural peppermint flavor (0.125 kg), natural menthol flavor (0.025 kg), and sucralose (0.020 kg) were blended separately for ten minutes. Magnesium stearate (0.075 kg), and zolpidem tartrate (0.034 kg) were blended for ten minutes and then passed through a #12 mesh screen. The blended mixtures were then added together and compressed into tablets. By using this procedure, the average particle size of the drug (i.e., zolpidem) in the quick-dissolving tablet is about 20 microns, as compared to a typical average drug particle size of from about 75 to about 100 microns. In addition, the average particle size of the drug in the quick-dissolving tablet is less than or equal to the average particle size of the carrier ingredients (e.g., gum base, binders, etc.).

A second zolpidem quick-dissolving tablet was made according to the formulation shown in Table 3 and the following procedure. Three separate blends of silicon dioxide with zolpidem, sodium carbonate, and sodium bicarbonate; mannitol and sorbitol; and polyethylene glycol, spearmint flavor, sucralose, magnesium stearate, crospovidone, and croscarmellose sodium were prepared. The three blends were screened separately and mixed to form a single blend. The single blend was then compressed into tablets after testing for content uniformity. By using this procedure, the average particle size of the drug (i.e., zolpidem) in the quick-dissolving tablet is about 20 microns, which is less than or equal to the average particle size of the carrier ingredients (e.g., gum base, binders, etc.). The unit weight for each tablet was 250 mg. The pH of the tablet was about 9.8 and remained stable. These tablets dissolve within about 5 minutes following sublingual administration.

TABLE 3

Zolpidem quick-dissolving tablet formulation.

| Material | Unit Quantity (mg) | Batch Quantity (g) |
| --- | --- | --- |
| Sodium Carbonate, NF | 17.000 | 357.000 |
| Sodium Bicarbonate USP | 23.000 | 483.000 |
| Zolpidem Tartrate, EP | 10.000 | 210.000 |
| Mannitol, USP | 40.000 | 840.000 |
| Sorbitol, NF | 103.500 | 2173.500 |
| Crospovidone, NF | 12.500 | 262.500 |
| Croscarmellose Sodium, NF | 12.500 | 262.500 |
| Polyethylene Glycol 3350, NF | 12.500 | 262.500 |
| Natural & Artificial Spearmint Flavor | 6.500 | 136.500 |
| Sucralose, NF | 1.000 | 21.000 |
| Silicon Dioxide, USP | 8.500 | 178.500 |
| Magnesium Stearate, NF | 3.000 | 63.000 |

The batch quantity formulation produces 21,000 unit doses.

Zolpidem Chewable Tablets:

A zolpidem chewable tablet was made according to the following procedure. Magnesium stearate USP (0.35 kg) was passed through a #20 mesh screen, and then loaded into a blender containing 0.810 kg mannitol granular USP, 9.569 kg sorbitol, and 0.020 kg stearic acid. The material was blended for 10 minutes. Zolpidem tartrate EP (0.034 kg) was ground with the magnesium stearate (0.02 kg) using a mortar and pestle. The remaining silicon dioxide, along with 0.228 kg magnesium stearate was added into the mortar while continuing to grind. The ground materials were transferred into a plastic bag, and the mortar was rinsed using 0.01 kg silicone dioxide, and transferred into the bag. The contents of the bag were then blended for five minutes.

Equal parts of the blended bag contents and the blended mannitol mixture were blended for an additional five minutes. This process was repeated until all the zolpidem and mannitol mixture had been blended together. Sodium carbonate (0.110 kg), sodium bicarbonate (0.570 kg), gum acacia (0.43 kg), xanthan gum (0.013 kg), and aspartame (0.072 kg) were then loaded into the blender with natural and artificial flavors and blended for ten minutes with 0.090 kg of silicon dioxide. The flavors used were as follows: natural and artificial grape flavor S.D. (0.215 kg), natural and artificial cherry flavor (0.108 kg), natural and artificial fruit punch flavor S.D. (0.180 kg), natural cherry WONF DURAROME® flavor (0.215 kg), and natural passion fruit type DURAROME® flavor (0.035 kg).

The blend was passed through a #12 mesh screen and then blended for an additional 15 minutes. Magnesium stearate (0.114 kg) was passed through a #20 mesh screen and added to the blend and blended for five minutes. The blend was collected and placed in plastic bags. Two silica gel desiccant bags were placed around the plastic bags to absorb ambient moisture. The blend was then compressed into tablets. By using this procedure, the average particle size of the drug (i.e., zolpidem) in the chewable tablet is about 20 microns, as compared to a typical average drug particle size of from about 75 to about 100 microns. In addition, the average particle size of the drug in the chewable tablet is less than or equal to the average particle size of the carrier ingredients (e.g., gum base, binders, etc.).

The zolpidem tablet composition of the present invention can be used, e.g., for treatment of insomnia. In certain instances, after the introduction of a chewable tablet into the mouth, the subject chews the chewable tablet as is normally done with any non-medicated type of chewable tablet at approximately an average rate of about 10 to about 45 chews per minute. In certain other instances, after the introduction of a dissolving tablet into the mouth, the subject holds the tablet underneath the tongue and either swallows while the tablet is dissolving or swallows after the tablet has dissolved.

A typical dosage form of the zolpidem tablet of the present invention is designed to produce an average plasma concentration of at least from about 20 to about 300 nanograms of zolpidem per milliliter of plasma. For example, a 5 mg zolpidem tablet can be designed to produce a mean peak plasma concentration within the range of from about 20 to about 100 nanograms of zolpidem per milliliter of plasma within about 5 minutes to about 2 hours. Similarly, a 10 mg zolpidem tablet can be designed to produce a mean peak plasma concentration within the range of from about 100 to about 300 nanograms of zolpidem per milliliter of plasma within about 5 minutes to about 2 hours.

The tablet compositions of the present invention provide a convenient, reliable, practical, and painless system for delivering zolpidem across the oral mucosa. Notably, the tablet compositions are capable of rapidly delivering zolpidem with low inter-subject variability in terms of maximum plasma concentration ($C_{max}$) and the time to reach the maximum plasma concentration ($T_{max}$) so that a therapeutically effective amount of zolpidem enters the bloodstream within about 30 minutes, 20 minutes, 15 minutes, 10 minutes, 5 minutes, or even within about 1-2 minutes after zolpidem is released from the carrier.

Example 4

Zolpidem Lozenge Compositions

This example illustrates the zolpidem lozenge compositions of the present invention.

Zolpidem can be formulated as a lozenge or candy composition as described above. In these embodiments, the unit dose or serving of the lozenge comprises from about 0.1 to about 100 milligrams (mg) zolpidem (as measured in its tartrate salt form), preferably from about 1 to about 50 mg, and more preferably from about 2 to about 25 mg. In other embodiments, the unit dose comprises from about 2 to about 20 mg zolpidem, preferably from about 2 to about 15 mg, and more preferably from about 2 to about 10 mg, e.g., about 2, 3, 4, 5, 6, 7, 8, 9, or 10 mg. In particularly preferred embodiments, the unit dose comprises a dose of zolpidem that is less than the dose typically used in commercial oral tablets, but possesses comparable or greater bioavailability and onset of therapeutic activity as well as lower inter-subject variability of drug absorption. In such embodiments, unit doses of from about 2 to about 5 mg zolpidem are preferred, with unit doses of about 4 mg zolpidem being particularly preferred. Extra zolpidem, for example, up to from about 10% to about 25% by weight, can be added as "overage" or as the amount that may be expected to be "washed away" and not otherwise released or absorbed during lozenge dissolution and/or mastication.

In another embodiment, the unit dose or serving of the lozenge comprises from about 0.81 to about 42 mg zolpidem in its base form, and more preferably from about 1.64 to about 20.5 mg. In other embodiments, the unit dose comprises from about 1.64 to about 16.4 mg zolpidem in its free base form, preferably from about 1.64 to about 12.3 mg, and more preferably from about 1.64 to about 8.2 mg, e.g., about 1.64, 2.46, 3.28, 4.1, 4.92, 5.78, 6.56, 7.38, or 8.2 mg. In additional embodiments, the unit dose comprises a mixture of zolpidem in free base form and salt form (e.g., zolpidem tartrate).

Given in weight percentages, the zolpidem lozenge composition comprises from about 0.001% to about 10.0% zolpidem (in whatever chosen form, measured as per its free base form), preferably from about 0.1% to about 8.0%, more preferably from about 1.0% to about 7.0%, and still more preferably from about 1.0% to about 5.5%. In some embodiments, about 4.5% zolpidem is used. One skilled in the art understands that the foregoing percentages will vary depending upon the particular source of zolpidem utilized, the amount of zolpidem desired in the final formulation, as well as on the particular release rate of zolpidem desired. The buffer system of the zolpidem lozenge composition provides for a final salivary pH in excess of at least about 7.8, preferably at least about 8.5, and more preferably at least about 9 (e.g., about 9-11).

A zolpidem lozenge was made according to the formulation shown in Table 4 and the following procedure. Three separate blends of silicon dioxide with zolpidem, sodium carbonate, and sodium bicarbonate; Pharmaburst; and spearmint flavor, sucralose, magnesium stearate, and croscarmellose sodium were prepared. The three blends were screened separately and mixed to form a single blend. The single blend was then compressed into lozenges after testing for content uniformity. By using this procedure, the average particle size of the drug (i.e., zolpidem) in the lozenge is about 20 microns, as compared to a typical average drug particle size of from about 75 to about 100 microns. In addition, the average particle size of the drug in the lozenge is less than or equal to the average particle size of the carrier ingredients (e.g., gum base, binders, etc.). The unit weight for each lozenge was 210 mg. The pH of the lozenge was about 9.8 and remained stable. These lozenges dissolve within about 2-3 minutes following sublingual administration.

TABLE 4

Zolpidem lozenge formulation.

| Material | Unit Quantity (mg) | Batch Quantity (g) |
|---|---|---|
| Sodium Carbonate, NF | 17.000 | 357.000 |
| Sodium Bicarbonate (Effer Soda) | 23.000 | 483.000 |
| Zolpidem Tartrate, EP | 10.000 | 210.000 |
| Pharmaburst B2 | 133.000 | 2793.000 |
| Croscarmellose Sodium | 10.000 | 210.000 |
| Natural & Artificial Spearmint Flavor | 6.500 | 136.500 |
| Sucralose, NF | 1.500 | 31.500 |
| Silicon Dioxide, USP | 5.500 | 115.500 |
| Magnesium Stearate, NF | 3.500 | 73.500 |

The batch quantity formulation produces 21,000 unit doses.

The zolpidem lozenge composition of the present invention can be used, e.g., for treatment of insomnia. In certain instances, after the introduction of a lozenge into the mouth, the subject holds the lozenge underneath the tongue and either swallows while the lozenge is dissolving or swallows after the lozenge has dissolved. The lozenges described herein have a very rapid rate of dissolution, and are capable of dissolving within about 2-3 minutes following sublingual administration.

A typical dosage form of the zolpidem lozenge of the present invention is designed to produce an average plasma concentration of at least from about 20 to about 300 nanograms of zolpidem per milliliter of plasma. For example, a 5 mg zolpidem lozenge can be designed to produce a mean peak plasma concentration within the range of from about 20 to about 100 nanograms of zolpidem per milliliter of plasma within about 5 minutes to about 2 hours. Similarly, a 10 mg zolpidem lozenge can be designed to produce a mean peak plasma concentration within the range of from about 100 to about 300 nanograms of zolpidem per milliliter of plasma within about 5 minutes to about 2 hours.

The lozenge compositions of the present invention provide a convenient, reliable, practical, and painless system for delivering zolpidem across the oral mucosa. Notably, the lozenge compositions are capable of very rapidly delivering zolpidem with low inter-subject variability in terms of maximum plasma concentration ($C_{max}$) and the time to reach the maximum plasma concentration ($T_{max}$) so that a therapeutically effective amount of zolpidem enters the bloodstream within about 30 minutes, 20 minutes, 15 minutes, 10 minutes, 5 minutes, or even within about 1-2 minutes after zolpidem is released from the carrier.

Example 5

Dissolution Profiles for Zolpidem Tablet and Lozenge Compositions

This example illustrates the mean dissolution profiles for a zolpidem quick-dissolving tablet made according to Table 3 and a zolpidem lozenge made according to Table 4.

The compositions tested were as follows:
1. Zolpidem quick-dissolving tablet (typically dissolves sublingually in about 5 minutes).
2. Zolpidem lozenge (typically dissolves sublingually in about 2-3 minutes).

The experimental conditions were as follows:
Method=USP
Apparatus=USP Apparatus II
Medium=Phosphate Buffer pH 6.8

Volume of the Medium=500 ml

Spindle Speed=25 rpm

Temperature=37° C.

Figure 2:
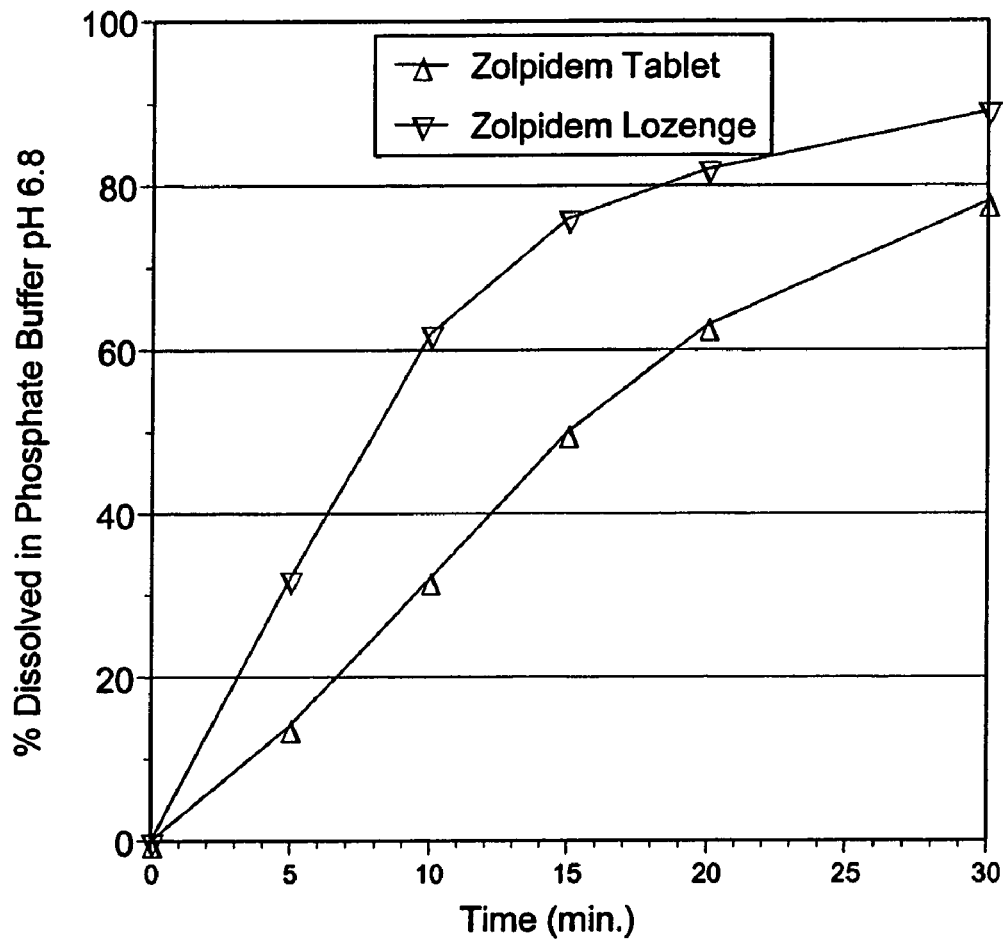
FIG. 2 shows the mean dissolution profiles for a zolpidem quick-dissolving tablet and zolpidem lozenge of the present invention.

Table 5 below shows the dissolution data and FIG. 2 shows the mean dissolution profiles for a zolpidem quick-dissolving tablet and zolpidem lozenge of the present invention at 5, 10, 15, 20, and 30 minutes in phosphate buffered medium (pH 6.8).

TABLE 5

Dissolution data for the zolpidem quick-dissolving tablet and zolpidem lozenge.

| Time (Min.) | Quick-Dissolving Tablet (% Dissolved, RSD[1]) | Lozenge (% Dissolved, RSD[1]) |
|---|---|---|
| 5 | 14.3, 17.7 | 32.4, 16.2 |
| 10 | 32.8, 14.8 | 61.7, 8.6 |
| 15 | 50.1, 14.6 | 75.7, 4.9 |
| 20 | 63, 15.9 | 82.1, 4.6 |
| 30 | 85.2, 7.9 | 88.6, 2.8 |

[1]RSD = Relative Standard Deviation

Example 6

Zolpidem Pharmacokinetic Studies

This example provides two studies illustrating the pharmacokinetic profile of the zolpidem tablets of the present invention as compared to a dose equivalent commercial oral tablet.

Zolpidem Sublingual Powdered Tablet vs. Ambien Oral Tablet:

To evaluate the pharmacokinetic profile of a sublingually administered zolpidem formulation, a 10 mg zolpidem powdered tablet buffered at a pH of 9.8 with 23 mg sodium bicarbonate and 17 mg sodium carbonate (Formulation A) was determined in eight healthy subjects (5 male, 3 female). Formulation A was administered under the subject's tongue and had a very rapid dissolution rate, i.e., within about 1 to about 3 minutes. The study performed was a fixed-sequence, open-label pharmacokinetic study in which subjects swallowed saliva at a rate of every 2, 5, or 10 minutes over a 10 minute period of time ("swallowing time"). For example, a 2 minute swallowing time refers to swallowing saliva every 2 minutes over a 10 minute period (i.e., 5 blocks of 2 minutes each); a 5 minute swallowing time refers to swallowing saliva every 5 minutes over a 10 minute period (i.e., 2 blocks of 5 minutes each); and a 10 minute swallowing time refers to swallowing saliva every 10 minutes over a 10 minute period (i.e., 1 block of 10 minutes). Serum blood samples were collected over an 8 hour period and the plasma was assayed for zolpidem levels, e.g., using high pressure liquid chromatography (HPLC)-tandem mass spectrometry (MS).

Figure 3:
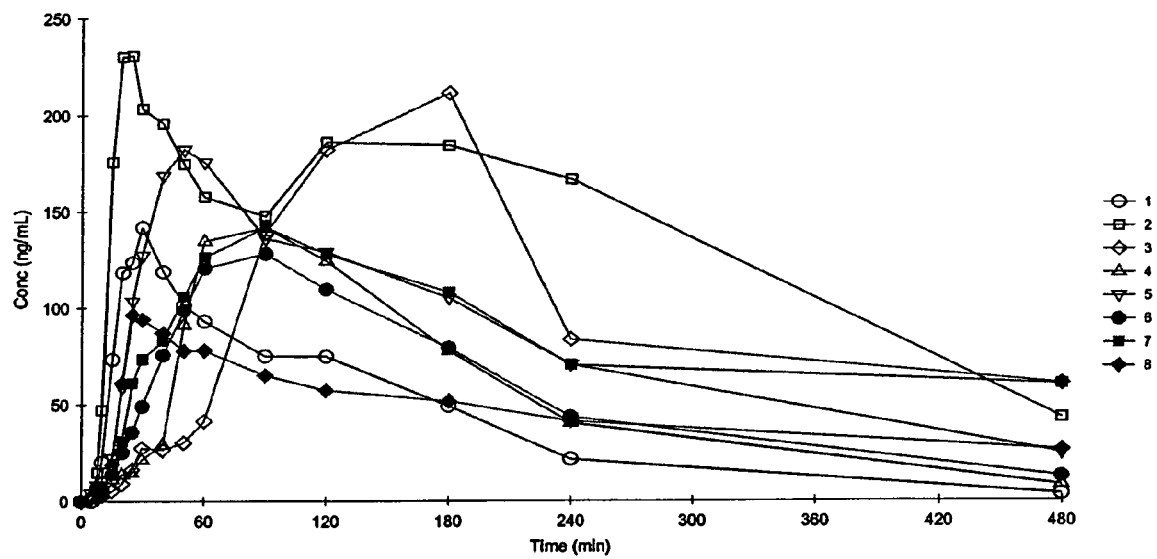
FIG. 3 shows the plasma concentration over time in each subject for Formulation A (zolpidem sublingual powdered tablet) at a 2 minute swallowing time.
Figure 4:
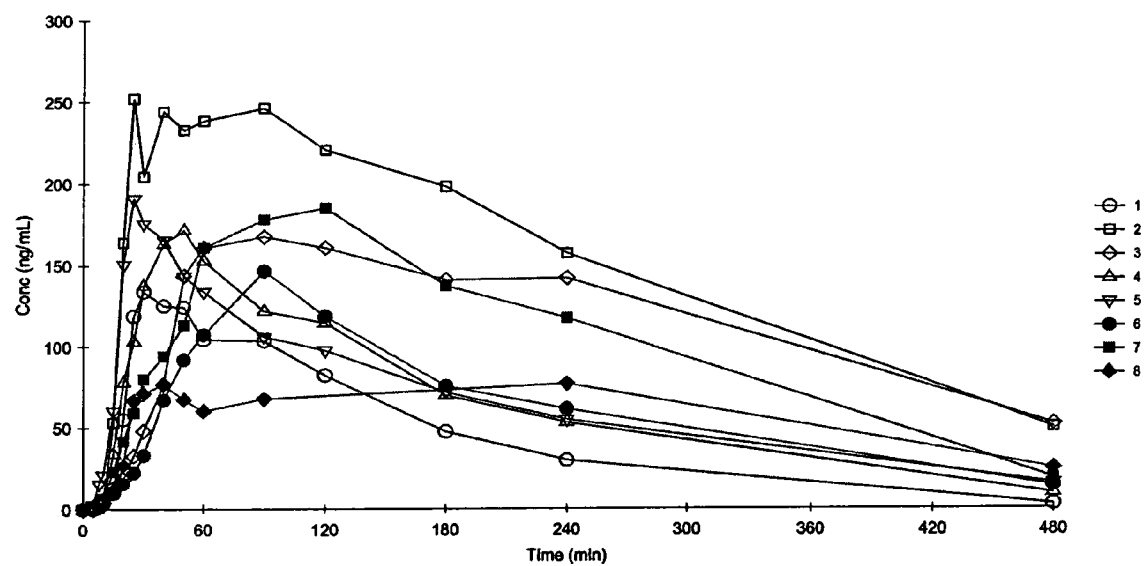
FIG. 4 shows the plasma concentration over time in each subject for Formulation A at a 5 minute swallowing time.
Figure 5:
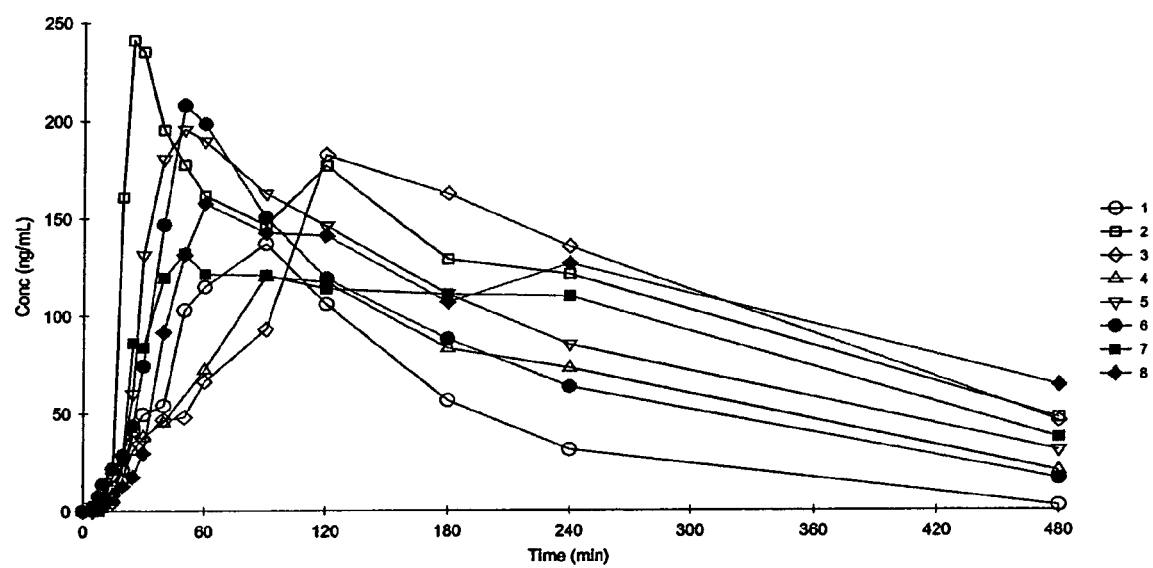
FIG. 5 shows the plasma concentration over time in each subject for Formulation A at a 10 minute swallowing time.

FIGS. 3-5 show the plasma concentration over time in each subject for Formulation A at swallowing times of 2, 5, and 10 minutes, respectively. Tables 6-8 below show the values for the pharmacokinetic parameters determined in each subject for Formulation A at swallowing times of 2, 5, and 10 minutes, respectively.

TABLE 6

Pharmacokinetic parameters for Formulation A at a 2 minute swallowing time.

| Subject | $T_{max}$ (min.) | $C_{max}$ (ng/ml) | $AUC_{0-8}$ (ng · hr/ml) |
|---|---|---|---|
| 1 | 30 | 142 | 317 |
| 2 | 25 | 231 | 1096 |
| 3 | 180 | 211 | 776 |
| 4 | 90 | 141 | 430 |
| 5 | 50 | 182 | 645 |
| 6 | 90 | 128 | 441 |
| 7 | 90 | 142 | 663 |
| 8 | 25 | 96 | 363 |
| Median (Range) | 70 (25-180) | | |
| Mean (CV %) | | 159 (28%) | 592 (44%) |

TABLE 7

Pharmacokinetic parameters for Formulation A at a 5 minute swallowing time.

| Subject | $T_{max}$ (min.) | $C_{max}$ (ng/ml) | $AUC_{0-8}$ (ng · hr/ml) |
|---|---|---|---|
| 1 | 30 | 134 | 350 |
| 2 | 25 | 252 | 1201 |
| 3 | 90 | 168 | 906 |
| 4 | 50 | 172 | 517 |
| 5 | 25 | 191 | 520 |
| 6 | 90 | 146 | 490 |
| 7 | 120 | 185 | 805 |
| 8 | 40 | 77 | 464 |
| Median (Range) | 45 (25-120) | | |
| Mean (CV %) | | 165 (30%) | 656 (44%) |

TABLE 8

Pharmacokinetic parameters for Formulation A at a 10 minute swallowing time.

| Subject | $T_{max}$ (min.) | $C_{max}$ (ng/ml) | $AUC_{0-8}$ (ng · hr/ml) |
|---|---|---|---|
| 1 | 390 | 137 | 364 |
| 2 | 25 | 241 | 913 |
| 3 | 120 | 183 | 824 |
| 4 | 90 | 120 | 508 |
| 5 | 50 | 196 | 728 |
| 6 | 50 | 208 | 587 |
| 7 | 50 | 131 | 708 |
| 8 | 60 | 158 | 826 |
| Median (Range) | 55 (25-120) | | |
| Mean (CV %) | | 172 (28%) | 682 (27%) |

Figure 6:
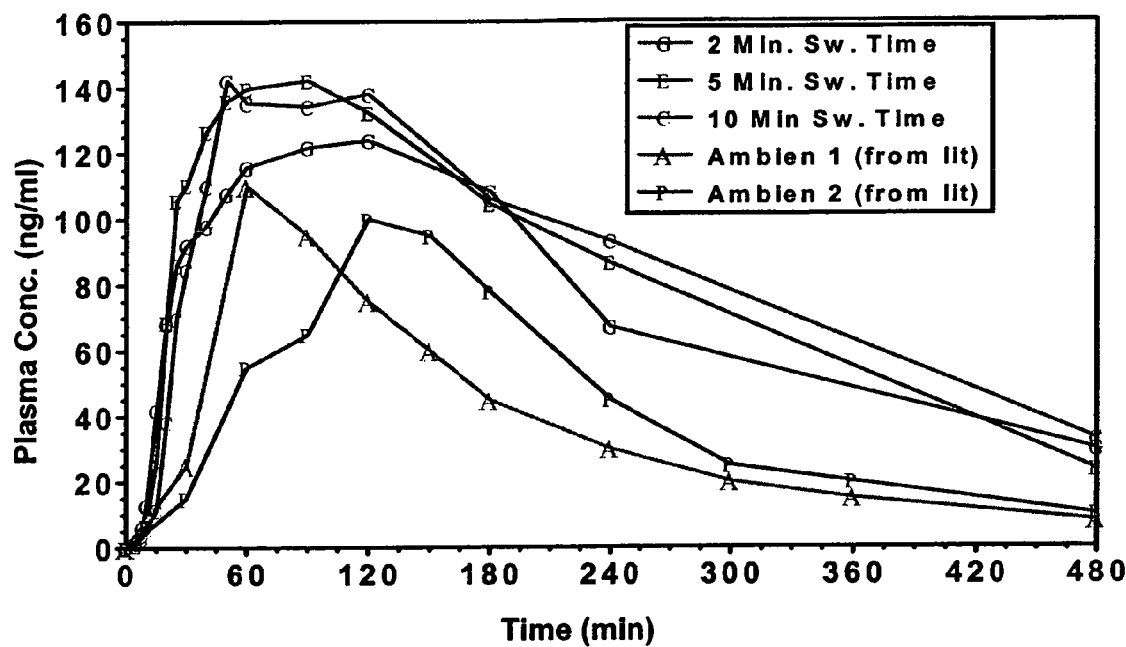
FIG. 6 shows the mean plasma concentration over time for Formulation A at the 3 different swallowing times and for Formulation B (PO Ambien®), which was obtained from the literature.

The pharmacokinetic results obtained for Formulation A were then compared to pharmacokinetic data obtained from the package insert and the literature for a dose equivalent Ambien® oral tablet formulation (Formulation B). FIG. 6 shows the mean plasma concentration over time for Formulation A (zolpidem sublingual powdered tablet) at the 3 different following times and for Formulation B (peroral (PO) Ambien®), which was obtained from the literature (Greenblatt et al., *Clin. Pharmacol. Ther.*, 64:553-561 (1998); Greenblatt et al., *Clin. Pharmacol. Ther.*, 64:661-671 (1998)). Table 9 below shows the means values for the pharmacokinetic parameters determined for Formulation A at the 3 different swallowing times and those for Formulation B from the literature (Greenblatt et al., *Clin. Pharmacol. Ther.*, 64:553-561 (1998)).

TABLE 9

Pharmacokinetic parameters for Formulation A and Formulation B.

| Formulation | $T_{max}$ (min.) | $C_{max}$ (ng/ml) | AUC (ng · hr/ml) |
|---|---|---|---|
| Formulation A (2 min. swallowing time) | 70 (25-180) | 159 (28%) | 592 (44%) |
| Formulation A (5 min. swallowing time) | 45 (25-120) | 165 (30%) | 656 (44%) |
| Formulation A (10 min. swallowing time) | 55 (25-120) | 172 (24%) | 682 (27%) |
| Formulation A (Cumulative) | 55 (25-180) | 166 (25%) | 644 (37%) |
| Formulation B | 102 (84-120) | 125 (12%) | 408 (12%) |

Values represent the mean.
The numbers in parentheses for $T_{max}$ represent the minimum and maximum values, respectively.
The numbers in parentheses for $C_{max}$ and AUC represent the coefficient of variation percent (CV %).

This study demonstrates that delivery of zolpidem across the oral mucosa produced mean plasma zolpidem concentrations that were from about 45% to about 67% greater than those observed for the commercial oral tablet during the 8 hour period following administration. In addition, peak plasma zolpidem concentrations were achieved within about 45 to about 70 minutes following sublingual administration, while peak plasma zolpidem concentrations were not achieved until 96 minutes (Ambien® package insert) or 102 minutes (Greenblatt et al., *Clin. Pharmacol. Ther.*, 64:553-561 (1998)) following commercial oral tablet administration. As such, the present study shows that zolpidem from the powdered sublingual tablet is rapidly absorbed and has substantially better bioavailability than the commercial oral tablet. The present study also shows that the improvement in bioavailability is independent of the swallowing time.

Figure 7:
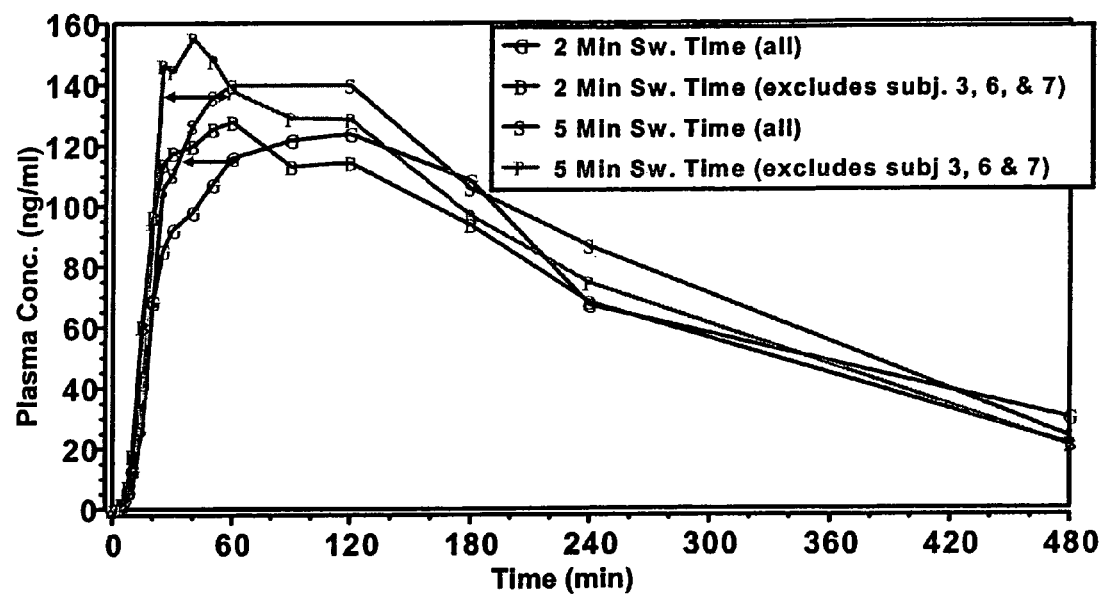
FIG. 7 shows the mean plasma concentration over time for Formulation A at swallowing times of 2 and 5 minutes using the data from all subjects or excluding the data from subjects 3, 6, and 7.

FIG. 7 shows the mean plasma concentration over time for Formulation A at swallowing times of 2 and 5 minutes using the data from all 8 subjects and the mean plasma concentration over time for Formulation A at swallowing times of 2 and 5 minutes excluding the data from subjects 3, 6, and 7, who apparently swallowed earlier than their scheduled swallowing time. Table 10 below shows the mean values for the pharmacokinetic parameters determined for Formulation A using the data from all 8 subjects or excluding the data from subjects 3, 6, and 7. When subjects who apparently did not comply with the study protocol were excluded from the analysis, peak plasma zolpidem concentrations for the remaining subjects were achieved within about 30 minutes rather than from about 45 to about 70 minutes following sublingual administration.

TABLE 10

Pharmacokinetic parameters for Formulation A with all subjects or excluding those who swallowed early.

| Swallowing Time | $T_{max}$ (min.) | $C_{max}$ (ng/ml) | AUC (ng · hr/ml) |
|---|---|---|---|
| 2 minutes (all subjects) | 70 (25-180) | 159 (28%) | 592 (44%) |
| 2 minutes (excluding subjects 3, 6, and 7) | 30 (25-90) | 159 (31%) | 570 (44%) |
| 5 minutes (all subjects) | 45 (25-120) | 165 (30%) | 656 (56%) |
| 5 minutes (excluding subjects 3, 6, and 7) | 30 (25-50) | 165 (40%) | 609 (55%) |

Values represent the mean.
The numbers in parentheses for $T_{max}$ represent the minimum and maximum values, respectively.
The numbers in parentheses for $C_{max}$ and AUC represent the coefficient of variation percent (CV %).

Figure 8:
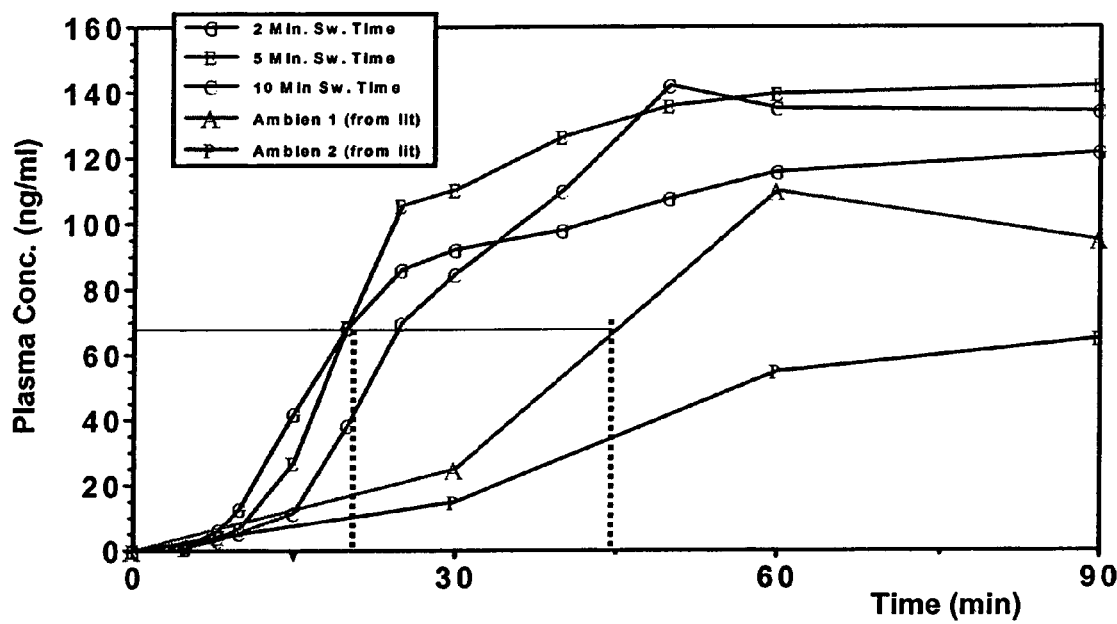
FIG. 8 is an expanded view of the first 90 minutes shown in FIG. 4.

FIG. 8 is an expanded view of the first 90 minutes shown in FIG. 6. In particular, FIG. 8 illustrates the estimated time for the onset of sleep in subjects taking Formulation A (left dotted line) compared to the time for the onset of sleep in subjects taking Formulation B (right dotted line). The mean plasma zolpidem concentration effective for inducing sleep onset is shown by the horizontal line in FIG. 8. Table 11 below shows the reported time for the onset of sleep during the daytime in each subject taking Formulation A at the 3 different swallowing times.

TABLE 11

Reported daytime sleep onset times for Formulation A.

| Subject | 2 min. swallowing time (min.) | 5 min. swallowing time (min.) | 10 min. swallowing time (min.) |
|---|---|---|---|
| 1 | 10 | 16 | 18 |
| 2 | 12 | 9 | 14 |
| 3 | 7 | 7 | 18 |
| 4 | 49 | 19 | 8 |
| 5 | 5 | 19 | 24 |
| 6 | 30 | 19 | 18 |
| 7 | 25 | 23 | 15 |
| 8 | 13 | 24 | 14 |
| Median | 12.5 | 19 | 16.5 |

This study demonstrates that the onset of sleep for subjects taking the zolpidem powdered sublingual tablet is substantially faster than that achieved with the commercial oral tablet. In fact, the onset of sleep for subjects taking the sublingual tablets of the present invention can be as early as within about 12.5 minutes following administration, which is more than 3 times faster than the onset of sleep for subjects taking the commercial oral tablet. One skilled in the art will appreciate that the onset of sleep observed during the daytime corresponds to the onset of sleep at night.

Furthermore, the pharmacokinetic profiles for sublingually administered zolpidem provide a softer and longer-lasting peak of zolpidem (see, FIG. 6), and thus resemble a pharmacokinetic profile for intravenously administered zolpidem. As a result, this infusion-like pharmacokinetic profile is equivalent to or even superior to the commercial oral tablet in reducing the time to onset of therapeutic activity, maintaining sleep (e.g., total sleep time, number of awakenings), enhancing sleep quality, eliminating the effect of food, and reducing any morning-after residual effects.

Zolpidem Slow-dissolving and Quick-dissolving Sublingual Tablets vs. Ambien Oral Tablet:

To further evaluate the pharmacokinetic profile of a sublingually administered zolpidem formulation, a 10 mg zolpidem slow-dissolving tablet made according to Table 2 (Formulation C) and a 10 mg zolpidem quick-dissolving tablet made according to Table 3 (Formulation D) was compared to a dose equivalent Ambien® oral tablet formulation (Formulation B) in eight healthy subjects. Formulation C (SL Tablet) was administered under the subject's tongue and had a slow dissolution rate, i.e., within about 10 minutes. Formulation D (FS Tablet) was administered under the subject's tongue and had a fast dissolution rate, i.e., within about 5 minutes. Formulation B (PO Ambien) was administered perorally with 180 ml of water. The study performed was a three-way crossover, fixed-sequence pharmacokinetic study in which subjects swallowed saliva at a rate of every 2 or 5 minutes over a 10 minute period of time ("swallowing time") for Formulations C and D. Serum blood samples were collected over a 12 hour period and the plasma was assayed for zolpidem levels, e.g., using high pressure liquid chromatography (HPLC)-tandem mass spectrometry (MS).

Figure 9:
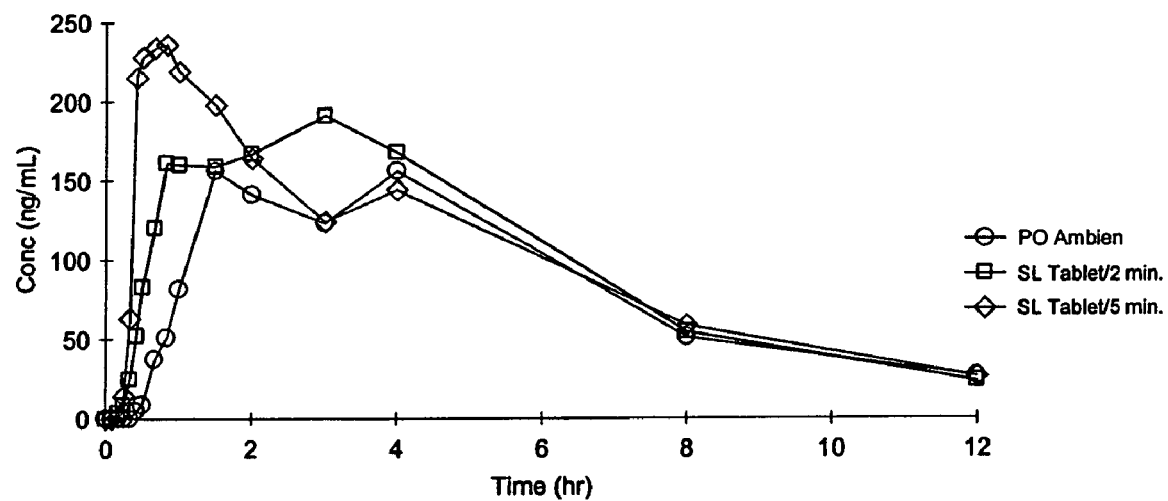
FIG. 9 shows a representative plasma concentration over time for Formulation C (SL Tablet) at swallowing times of 2 and 5 minutes and for Formulation B.
Figure 10:
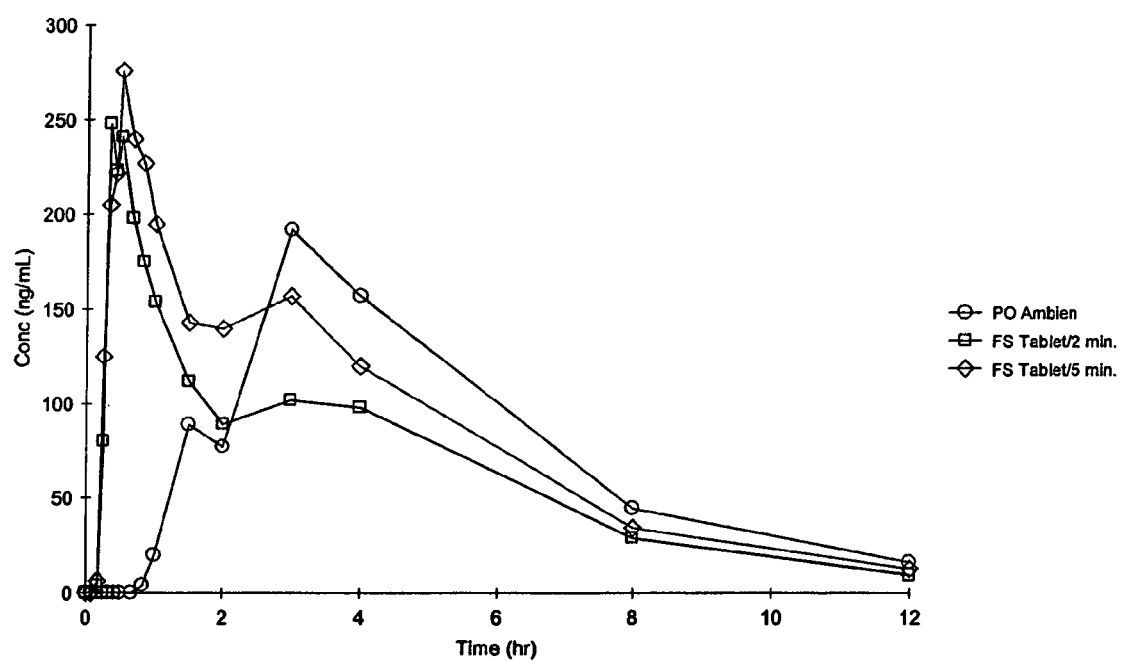
FIG. 10 shows a representative plasma concentration over time for Formulation D (FS Tablet) at swallowing times of 2 and 5 minutes and for Formulation B.

FIG. 9 shows the mean plasma concentration over time for Formulation C (SL Tablet) at swallowing times of 2 and 5 minutes and for Formulation B (PO Ambien). Likewise, FIG. 10 shows the mean plasma concentration over time for Formulation D (FS Tablet) at swallowing times of 2 and 5 minutes and for Formulation B (PO Ambien). This study demonstrates that delivery of zolpidem across the oral mucosa produced peak plasma zolpidem concentrations at a substantially earlier period in time and at a substantially higher level following sublingual administration than observed for the commercial oral tablet administration. As such, the present study shows that zolpidem from both dissolving tablets is rapidly absorbed and has substantially better bioavailability than the commercial oral tablet. Furthermore, the onset of sleep for subjects taking either zolpidem dissolving tablet is substantially faster than that achieved with the commercial oral tablet. The present study also shows that the improvement in bioavailability is independent of the swallowing time and the formulation of the dissolving tablet.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating insomnia, comprising the steps of:
administering to a subject a solid pharmaceutical composition comprising zolpidem in an amount from about 1 mg to about 5 mg, a carbonate buffer, and a bicarbonate buffer,
wherein zolpidem is absorbed across the subject's oral mucosa,
wherein the carbonate buffer and bicarbonate buffer are present in a carbonate:bicarbonate weight ratio of about 1:1 to about 1:10 and raise the pH of saliva to a pH of about 7.8 or greater, and
wherein at least 75% of the solid pharmaceutical composition dissolves within about 10 minutes or less within an oral cavity following administration.

2. The method of claim 1, wherein the solid pharmaceutical composition further comprises a binder and a disintegrating agent.

3. The method of claim 1, wherein the solid pharmaceutical composition dissolves within about 10 minutes or less within said oral cavity following administration.

4. The method of claim 1, wherein the solid pharmaceutical composition dissolves within about 1-3 minutes within said oral cavity following administration.

5. The method of claim 1, wherein the solid pharmaceutical composition dissolves within about 2-3 minutes within said oral cavity following administration.

6. The method of claim 1, wherein the solid pharmaceutical composition is administered sublingually.

7. The method of claim 1, wherein the oral mucosa is selected from the group consisting of sublingual mucosa, buccal mucosa, gingival mucosa, palatal mucosa, and lining of the lips.

8. The method of claim 1, wherein a mean peak plasma concentration of zolpidem between about 20 to about 100 ng/mL is produced within about 30 minutes.

9. The method of claim 1, wherein a therapeutically effective amount of zolpidem enters the bloodstream within about 30 minutes.

10. The method of claim 1, wherein the carbonate buffer and bicarbonate buffer are present in a carbonate:bicarbonate weight ratio of about 1:1 to about 1:5.

11. The method of claim 1, wherein the carbonate buffer and bicarbonate buffer are present in a carbonate:bicarbonate weight ratio of about 1:1 to about 1:2.

12. The method of claim 1, wherein the solid pharmaceutical composition is a lozenge.

13. The method of claim 1, wherein the solid pharmaceutical composition is a tablet.

14. A pharmaceutical composition comprising:
about 1 mg to about 5 mg of zolpidem;
a carbonate buffer; and
a bicarbonate buffer,
wherein the carbonate buffer and bicarbonate buffer are present in a carbonate:bicarbonate weight ratio of about 1:1 to about 1:10 and are adapted to raise the pH of saliva to about 7.8 or greater following administration, and
wherein the solid pharmaceutical composition is adapted to dissolve by at least 75% within about 10 minutes or less within an oral cavity following administration.

15. The pharmaceutical composition of claim 14, wherein the pharmaceutical composition is a solid pharmaceutical composition.

16. The pharmaceutical composition of claim 14, wherein the carbonate buffer and bicarbonate buffer are present in a carbonate:bicarbonate weight ratio of about 1:1 to about 1:5.

17. The pharmaceutical composition of claim 14, wherein the carbonate buffer and bicarbonate buffer are present in a carbonate:bicarbonate weight ratio of about 1:1 to about 1:2.

18. The pharmaceutical composition of claim 15, further comprising a binder and a disintegrating agent.

19. The pharmaceutical composition of claim 15, wherein the solid pharmaceutical composition is a lozenge.

20. The pharmaceutical composition of claim 15, wherein the solid pharmaceutical composition is a tablet.

21. The pharmaceutical composition of claim 14, wherein the carbonate buffer is selected from the group consisting of sodium carbonate, potassium carbonate, calcium carbonate, ammonium carbonate, and magnesium carbonate.

22. The pharmaceutical composition of claim 14, wherein the bicarbonate buffer is selected from the group consisting of sodium bicarbonate, potassium bicarbonate, calcium bicarbonate, ammonium bicarbonate, and magnesium bicarbonate.

23. The pharmaceutical composition of claim 14, wherein the bicarbonate buffer is dessicant-coated sodium bicarbonate.

24. The method of claim 1, wherein a therapeutically effective amount of zolpidem enters the bloodstream within about 20 minutes.

25. The pharmaceutical composition of claim 14, wherein the solid pharmaceutical composition is adapted to deliver a therapeutically effective amount of zolpidem into the bloodstream within about 30 minutes.

26. The pharmaceutical composition of claim 14, wherein the solid pharmaceutical composition is adapted to deliver a therapeutically effective amount of zolpidem into the bloodstream within about 20 minutes.

* * * * *

UNITED STATES PATENT AND TRADEMARK OFFICE
CERTIFICATE OF CORRECTION

| | |
|---|---|
| PATENT NO. | : 7,658,945 B2 |
| APPLICATION NO. | : 11/060641 |
| DATED | : February 9, 2010 |
| INVENTOR(S) | : Nikhilesh N. Singh |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 788 days.

Signed and Sealed this

Thirtieth Day of November, 2010

David J. Kappos
*Director of the United States Patent and Trademark Office*